(12) United States Patent
Winkler-Ebner et al.

(10) Patent No.: US 12,730,553 B2
(45) Date of Patent: Sep. 8, 2026

(54) ULTRASOUND SYSTEM FOR DISPLAYING ULTRASOUND PREVIEW IMAGES BASED ON A GAZE LOCATION OF A USER

(71) Applicant: GE Precision Healthcare LLC, Waukesha, WI (US)

(72) Inventors: Heinz Winkler-Ebner, Tiefgraben (AT); Balint Czupi, Seewalchen am Attersee (AT)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 19/005,251

(22) Filed: Dec. 30, 2024

(65) Prior Publication Data

US 2026/0186641 A1 Jul. 2, 2026

(51) Int. Cl.

*G06F 3/04845* (2022.01)
*G06F 3/01* (2006.01)
*G06F 3/0485* (2022.01)
*G16H 30/40* (2018.01)

(52) U.S. Cl.

CPC .......... *G06F 3/04845* (2013.01); *G06F 3/013* (2013.01); *G06F 3/0485* (2013.01); *G16H 30/40* (2018.01)

(58) Field of Classification Search

CPC .... G06F 3/04845; G06F 3/013; G06F 3/0485; G16H 30/40

See application file for complete search history.

(56) References Cited

U.S. PATENT DOCUMENTS 5,850,211 A * 12/1998 Tognazzini .............. G06F 3/013 345/158
7,501,995 B2 3/2009 Morita et al.
9,720,238 B2 8/2017 Munger et al.
9,967,475 B2 5/2018 Schneider et al.
10,373,592 B2 8/2019 Tall et al.
11,830,614 B2 11/2023 Huynh
2010/0231504 A1 9/2010 Bloem et al.
2015/0002490 A1 1/2015 Han et al.

(Continued)

FOREIGN PATENT DOCUMENTS

CN 116616814 A 8/2023

OTHER PUBLICATIONS

Halwani et al., Enhancing Zoom and Pan in Ultrasound Machines with a Multimodal Gaze-Based Interface, May 6-11, 2017.

(Continued)

*Primary Examiner* — Afroza Chowdhury
(74) *Attorney, Agent, or Firm* — SPQ IP LLC

(57) ABSTRACT

Various systems and methods are provided for displaying ultrasound preview images based on a gaze location of a user. An ultrasound system may display a set of ultrasound preview images on a display of the ultrasound system. The ultrasound system may determine a gaze location of a user on the display of the ultrasound system. The ultrasound system may determine an ultrasound preview image that corresponds to the gaze location of the user on the display of the ultrasound system. The ultrasound system may increase a size of the ultrasound preview image based on determining the ultrasound preview image that corresponds to the gaze location of the user on the display of the ultrasound system.

21 Claims, 19 Drawing Sheets

(56) References Cited

U.S. PATENT DOCUMENTS

| | | | | |
|---|---|---|---|---|
| 2015/0095844 | A1* | 4/2015 | Cho | G06F 3/0304<br>715/784 |
| 2015/0128075 | A1* | 5/2015 | Kempinski | G06F 3/012<br>715/765 |
| 2015/0169052 | A1 | 6/2015 | Kramer | |
| 2021/0098112 | A1 | 4/2021 | Gagnon | |
| 2024/0086059 | A1 | 3/2024 | Huffman et al. | |
| 2024/0164757 | A1* | 5/2024 | Errico | A61B 8/463 |
| 2024/0237969 | A1* | 7/2024 | Kano | A61B 8/12 |

OTHER PUBLICATIONS

Halwani, An Investigation of Multi-Modal Gaze-Supported Zoom and Pan Interactions in Ultrasound Machines, Oct. 2017.

* cited by examiner

ULTRASOUND SYSTEM FOR DISPLAYING ULTRASOUND PREVIEW IMAGES BASED ON A GAZE LOCATION OF A USER

TECHNICAL FIELD

The present disclosure relates to an ultrasound system for displaying ultrasound preview images based on a gaze location of a user. More specifically, the present disclosure relates to an ultrasound system that determines a gaze location of a user on a display of the ultrasound system, determines an ultrasound preview image that corresponds to the gaze location of the user on the display of the ultrasound system, and increases a size of the ultrasound preview image.

BACKGROUND

An ultrasound system may include, among other things, an ultrasound probe, a display, and a user input device. During an exam of a subject, a user may operate the ultrasound probe to acquire ultrasound data of the subject. For example, the ultrasound probe may acquire ultrasound data by transmitting ultrasound signals towards a region of interest of a subject and receiving echo signals reflected by, or back-scattered from, the region of interest of the subject. The display may display ultrasound images that are generated by the ultrasound system based on the ultrasound data. The user input device may allow the user to interact with a displayed ultrasound image.

The ultrasound system may store, or access, a large number of ultrasound images corresponding to previous exams of the subject and/or of other subjects. Further, the ultrasound system may permit the user to navigate through the ultrasound images to select a particular image for display. To do so, the ultrasound system may display ultrasound preview images corresponding to the ultrasound images of the exams. The ultrasound preview images may include relatively smaller sizes and/or resolutions than as compared to the corresponding ultrasound images. In this way, the ultrasound system may display a relatively larger number of ultrasound preview images concurrently on the display. However, the user of the ultrasound system might find it difficult to ascertain the content of a particular ultrasound preview image because of the relatively small size and resolution of the ultrasound preview image. Thus, the user might be required to interact with the user input device to select and view a particular ultrasound preview image. Based on this manual selection, the ultrasound system may display an ultrasound image corresponding to the selected ultrasound preview image.

In some cases, the user input device may be cumbersome, non-intuitive, and/or inefficient for quickly navigating through the ultrasound preview images and selecting a desired ultrasound image for display. Accordingly, the user might find it cumbersome, non-intuitive, inefficient, etc., to manually navigate through the ultrasound preview images. In this way, processor and/or memory resources of the ultrasound system might be consumed based on extensive user inputs received via the user input device to navigate through the ultrasound preview images. In other cases, the user might be incapable of manually interacting with the user input device. For instance, during an exam, the user might be holding the ultrasound probe, might have ultrasound gel on his or her hands, or the like. Accordingly, there is a need for an ultrasound system that allows a user to quickly and efficiently ascertain the content of ultrasound preview images.

SUMMARY

This summary introduces concepts that are described in more detail in the detailed description. It should not be used to identify essential features of the claimed subject matter, nor to limit the scope of the claimed subject matter.

In an aspect, an ultrasound system may include transducer elements configured to generate ultrasound signals, transmit the ultrasound signals towards a region of interest of a subject, and receive echo signals reflected by the region of interest of the subject; an acoustic matching layer configured to match an impedance differential between the transducer elements and the subject; a backing layer configured to attenuate the ultrasound signals transmitted by the transducer elements; a memory configured to store instructions; and one or more processors configured to execute the instructions to: display a set of ultrasound preview images on a display of the ultrasound system; determine a gaze location of a user on the display of the ultrasound system; determine an ultrasound preview image that corresponds to the gaze location of the user on the display of the ultrasound system; and increase a size of the ultrasound preview image based on determining the ultrasound preview image that corresponds to the gaze location of the user on the display of the ultrasound system.

In another aspect, a method may include displaying a set of ultrasound preview images on a display of the ultrasound system; determining a gaze location of a user on the display of the ultrasound system; determining an ultrasound preview image that corresponds to the gaze location of the user on the display of the ultrasound system; and increasing a size of the ultrasound preview image based on determining the ultrasound preview image that corresponds to the gaze location of the user on the display of the ultrasound system.

In yet another aspect, a non-transitory computer-readable medium may store instructions that, when executed by one or more processors, cause the one or more processors to: display a set of ultrasound preview images on a display of the ultrasound system; determine a gaze location of a user on the display of the ultrasound system; determine an ultrasound preview image that corresponds to the gaze location of the user on the display of the ultrasound system; and increase a size of the ultrasound preview image based on determining the ultrasound preview image that corresponds to the gaze location of the user on the display of the ultrasound system.

DETAILED DESCRIPTION

Figure 1:
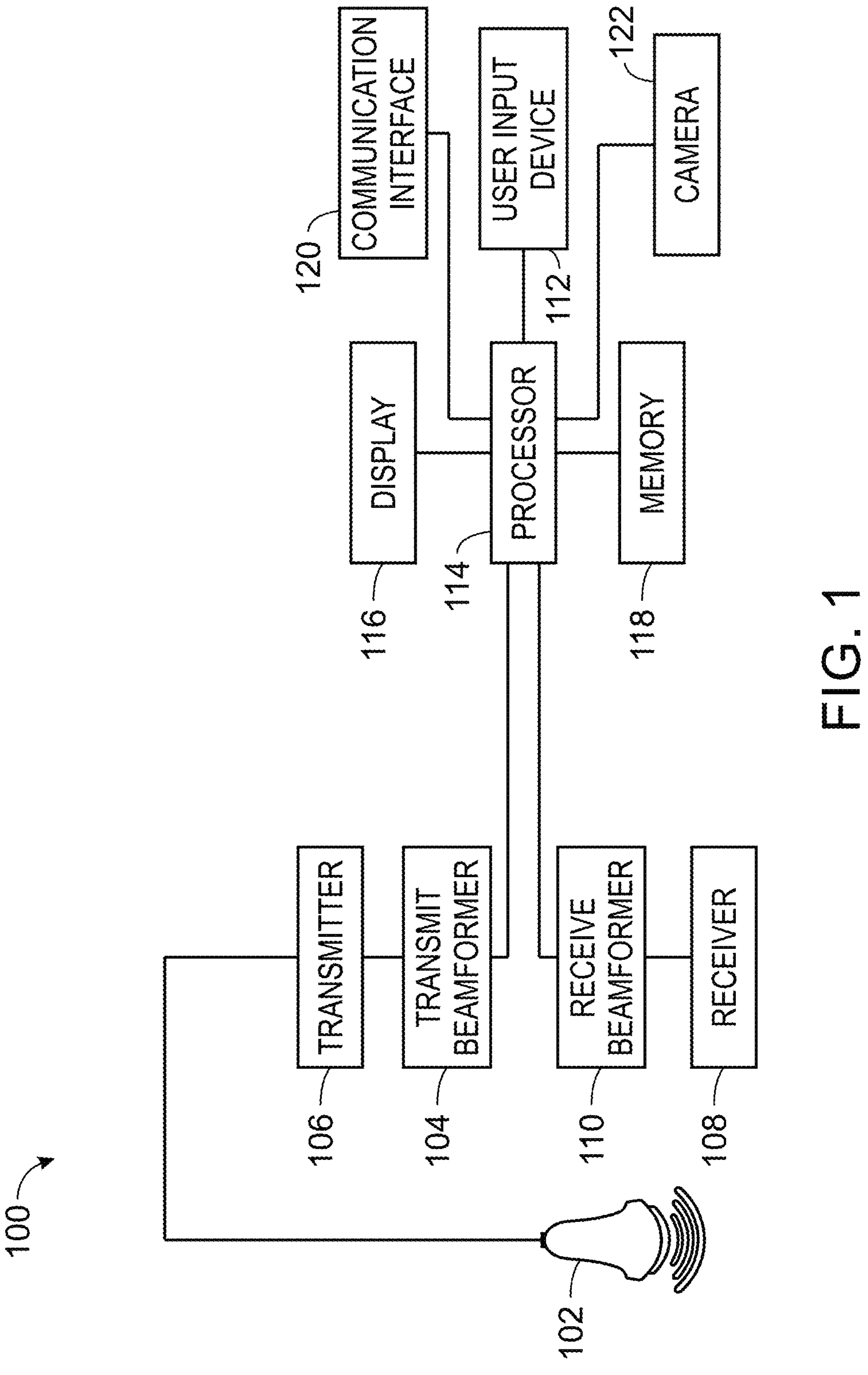
FIG. 1 is a diagram of example components of an ultrasound system for displaying ultrasound preview images based on a gaze location of a user.

As addressed above, a user input device of an ultrasound system may be cumbersome and/or non-intuitive for quickly navigating through the ultrasound preview images. Accordingly, the user might find it cumbersome, tedious, inefficient, etc., to manually navigate through the ultrasound preview images and select various ultrasound preview images using the user input device. In this way, processor and/or memory resources of the ultrasound system might be consumed based on extensive user inputs received via the user input device. In other cases, the user might be incapable of manually interacting with the user input device. For instance, during an exam, the user might be holding the ultrasound probe, might have ultrasound gel on his or her hands, or the like. Accordingly, there is a technical need for an ultrasound system that allows a user to quickly and efficiently ascertain the content of ultrasound preview images.

Some embodiments herein provide an ultrasound system that displays ultrasound preview images based on a gaze location of a user. According to an embodiment, the ultrasound system may display a set of ultrasound preview images on a display of the ultrasound system, determine a gaze location of a user on the display of the ultrasound system, determine an ultrasound preview image that corresponds to the gaze location of the user on the display of the ultrasound system, and increase a size of the ultrasound preview image based on determining the ultrasound preview image that corresponds to the gaze location of the user on the display of the ultrasound system. In this way, the ultrasound system may increase the size of an ultrasound preview image that a user is viewing in order to allow the user to more readily ascertain the content of the ultrasound preview image. Further, in this way, the user may select the ultrasound preview image for enhanced display by merely viewing the ultrasound preview image instead of manually interacting with a user input device.

According to another embodiment, the ultrasound system may display a set of ultrasound preview images in a list on a display of the ultrasound system, determine that a gaze location of a user on the display of the ultrasound system corresponds to an end of the list, and scroll through the set of ultrasound preview images in the list based on determining that the gaze location of the user on the display of the ultrasound system corresponds to the end of the list.

According to another embodiment, the ultrasound system may display a set of ultrasound preview images on a display of an ultrasound system, determine a gaze location of a user on the display of the ultrasound system, determine an ultrasound preview image that corresponds to the gaze location of the user on the display of the ultrasound system, and display an ultrasound video corresponding to the ultrasound preview image.

In this way, some embodiments herein provides a technical improvement in the technical field of ultrasound imaging and a technical improvement to ultrasound systems by permitting a user to navigate through and select a particular ultrasound preview image for viewing by viewing the display of the ultrasound system. In this way, the user is not required to manually interact with a user input device of the ultrasound system to navigate through and select a particular ultrasound preview image, which improves the efficiency and speed of navigating through and selecting a particular ultrasound preview image and reduces processor and/or memory resource consumption.

FIG. 1 is a diagram of example components of an ultrasound system 100 for displaying ultrasound preview images based on a gaze location of a user. As shown in FIG. 1, the ultrasound system 100 may include an ultrasound probe 102, a transmit beamformer 104, a transmitter 106, a receiver 108, a receive beamformer 110, a user input device 112, a processor 114, a display 116, a memory 118, a communication interface 120, and a camera 122. The foregoing components may be connected via wired or wireless connections.

The ultrasound probe 102 may be configured to acquire ultrasound data. For example, the ultrasound probe 102 may be a linear probe, a phase array probe, a curved linear probe coupled with a position tracking system, a mechanically steered linear array transducer, a phased array transducer, a curved linear array transducer, an electronically steered 2D transducer array, an electronic 3D (e3D) probe, an electronic 4d (e4D) probe, a low profile wearable patch version of any of the foregoing probes, or the like. According to an embodiment, the ultrasound probe 102 may be configured to generate ultrasound signals, emit the ultrasound signals towards the region of interest of a subject, receive echo ultrasound signals that are back-scattered from the region of interest of the subject, generate ultrasound data based on the echo ultrasound signals, and output the ultrasound data.

The transmit beamformer 104 may be configured to apply delay times to electrical signals provided to elements of the ultrasound probe 102 to focus corresponding ultrasound signals at the region of interest. The transmitter 106 may be configured to transmit electrical signals to the elements of the ultrasound probe 102 to drive the elements of the ultrasound probe 102 to emit ultrasound signals towards the region of interest. The elements of the ultrasound probe 102 may be configured to receive the electrical signals from the transmitter 106, convert the electrical signals into ultrasound signals, and emit the ultrasound signals towards the region of interest. The elements of the ultrasound probe 102 may be configured to receive echo ultrasound signals that are back-scattered by the region of interest, convert the echo ultrasound signals into electrical signals, and provide the electrical signals to the receiver 108. The receiver 108 may be configured to receive electrical signals from the elements, and provide the electrical signals to the receive beamformer

110. The receive beamformer 110 may apply delay times to the electrical signals received from the elements of the ultrasound probe 102.

The user input device 112 may be configured to receive a user input, and provide the user input to the processor 114. The user input device 112 may be a user interface. For example, the user input device 112 may be a touch screen display, a keyboard, a keypad, a mouse, a button, a switch, a microphone, or the like. Additionally, or alternatively, the user input device 112 may be configured to sense information. For example, the user input device 112 may sense information from an electro-magnetic positioning system, an inertial measurement system, an accelerometer, a gyroscope, an actuator, or the like.

The processor 114 may be configured to perform the operations as described herein. For example, the processor 114 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. The processor 114 may be implemented in hardware, firmware, or a combination of hardware and software. The processor 114 may include one or more processors 114 configured to perform the operations described herein. For example, a single processor 114 may be configured to perform all of the operations described herein. Alternatively, multiple processors 114, collectively, may be configured to perform all of the operations described herein, and each of the multiple processors 114 may be configured to perform a subset of the operations descried herein. For example, a first processor 114 may perform a first subset of the operations described herein, a second processor 114 may be configured to perform a second subset of the operations described herein, etc.

The processor 114 may be configured to control the ultrasound probe 102 to acquire ultrasound data. The processor 114 may be configured to control which of the elements of the ultrasound probe 102 are active, and control the shape of a beam emitted from the ultrasound probe 102. The processor 114 may generate ultrasound images for display. For example, the processor 114 may generate B-mode images, color Doppler images, M-mode images, color M-mode images, or the like. The ultrasound images may be 3D images, 2D images, single plane images, bi-plane images, three-plane images, multi-plane images, or the like. The ultrasound images may correspond to various anatomical planes (e.g., sagittal, coronal, and transverse) of the region of interest.

The display 116 may be configured to display information. For example, the display 116 may be a monitor, an LED display, a cathode ray tube, a projector display, a touch-screen, tablet computer, mobile phone, or the like. The display 116 may display ultrasound images based on the ultrasound data in real-time. For example, the display 116 may display the ultrasound images within one second, two seconds, five seconds, etc., of the ultrasound data being acquired by the ultrasound probe 102. The display 116 may be configured to display ultrasound preview images.

The memory 118 may be configured to store information and/or instructions for use by the processor 114. The memory 118 may be a non-transitory computer-readable medium. For example, the memory 118 may be a random access memory (RAM), a read only memory (ROM), and/or another type of dynamic or static storage device (e.g., a flash memory, a magnetic memory, and/or an optical memory) that stores information and/or instructions for use by the processor 114. The memory 118 may be configured to store instructions that, when executed by the processor 114, cause the processor 114 to perform the operations described herein. According to an embodiment, the memory 118 may store ultrasound images and ultrasound preview images corresponding to the ultrasound images. For example, the memory 118 may be a picture archiving and communication system (PACS).

The communication interface 120 may be configured to enable the processor 114 to communicate with other systems, such as via a wired connection, a wireless connection, or a combination of wired and wireless connections. For example, the communication interface 120 may include an Ethernet interface, an optical interface, a coaxial interface, an infrared interface, a radio frequency (RF) interface, a universal serial bus (USB) interface, a Wi-Fi interface, a cellular network interface, or the like.

The camera 122 may be configured to acquire gaze location information of a user of the ultrasound system 100. For example, the camera 122 may be a digital camera, a video camera, a complementary metal-oxide-semiconductor (CMOS) camera, an infrared camera, or the like. According to an embodiment, the camera 122 may be integrated with the ultrasound system 100. For example, the camera 122 may be mounted in a bezel of the display 116. Alternatively, the camera 122 may be external to the ultrasound system 100, and may connect to the ultrasound system 100. The camera 122 may acquire the gaze location information of the user by tracking the eyes of the user.

The number and arrangement of the components of the ultrasound system 100 shown in FIG. 1 are provided as an example. In practice, the ultrasound system 100 may include additional components, fewer components, different components, or differently arranged components than those shown in FIG. 1. Additionally, or alternatively, a set of components (e.g., one or more components) of the ultrasound system 100 may perform one or more functions described as being performed by another set of components of the ultrasound system 100.

Figure 2:
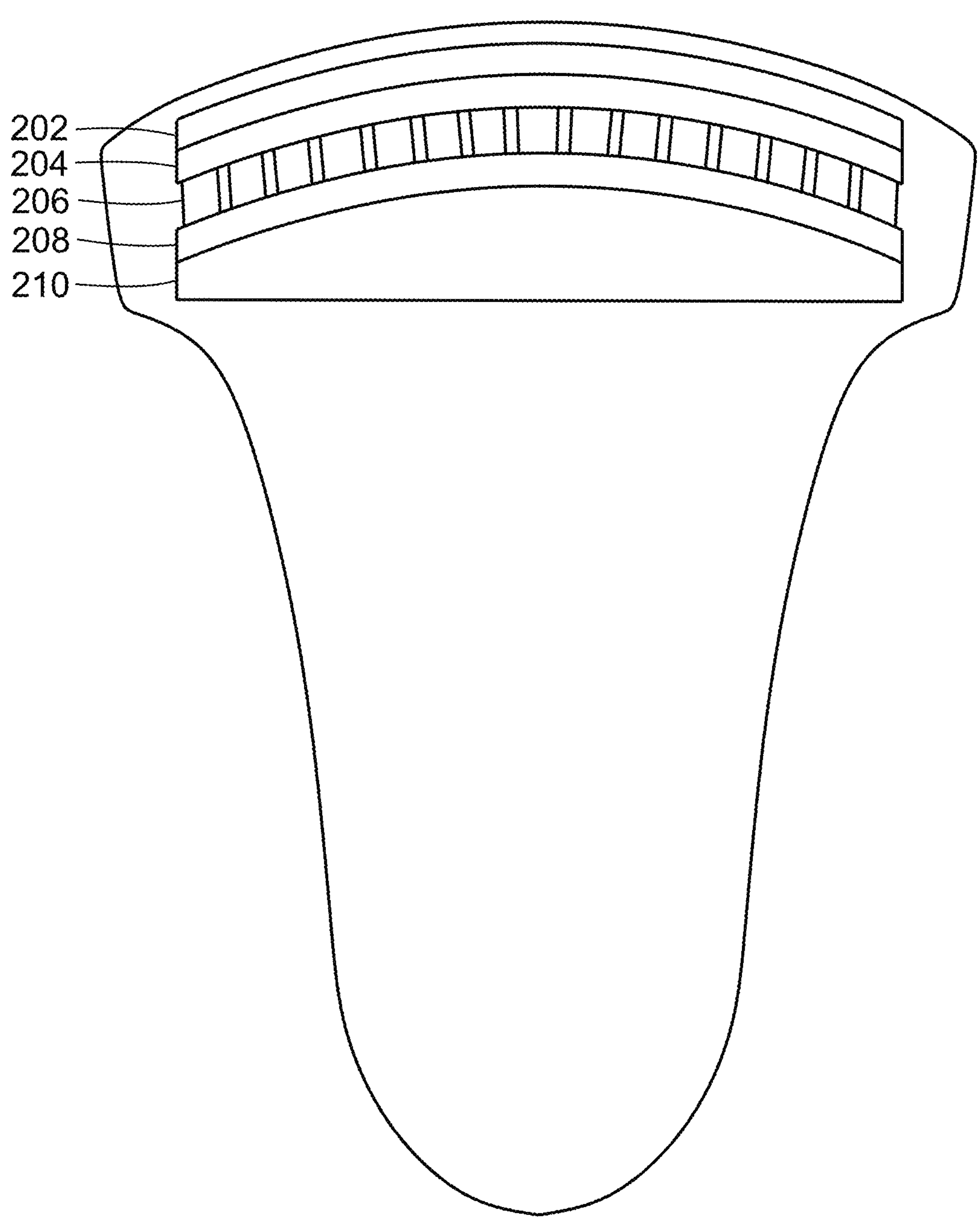
FIG. 2 is a diagram of an example ultrasound probe of the ultrasound system for displaying ultrasound preview images based on a gaze location of a user.

FIG. 2 is a diagram of an example ultrasound probe 102 of the ultrasound system 100 for displaying ultrasound preview images based on a gaze location of a user. As shown in FIG. 2, the ultrasound probe 102 may include a lens 202, an acoustic matching layer 204, transducer elements 206, an acoustic dematching layer 208, and a backing layer 210.

According to an embodiment, the lens 202 may be configured to direct an ultrasound signal towards the region of interest of the subject. For example, the lens 202 may be silicone, epoxy, rubber, or the like. According to an embodiment, the acoustic matching layer 204 may be configured to facilitate matching of an impedance differential that may exist between the relatively high impedance transducer elements 206 and the relatively low impedance subject. For example, the acoustic matching layer 204 may be graphite, plastic, resin, or the like. According to an embodiment, the transducer elements 206, respectively, may be configured to receive an element specific transmit signal, deform based on the element specific transmit signal, generate an ultrasound signal based on the deformation, and transmit the ultrasound signal towards a region of interest. Additionally, or alternatively, the transducer elements 206 may be configured to receive an echo signal reflected by or backscattered from the region of interest, deform based on the echo signal, generate an electrical signal based on the deformation, and transmit the electrical signal. For example, the transducer elements 206 may be piezoelectric materials, such as $Pb(Mg_{1/3}Nb_{2/3})O_3$—$PbTiO_3$ ("PMN-PT"), $Pb(In_{1/2}Nb_{1/2})O_3$—$Pb(Mg_{1/}$ ${}_3Nb_{2/3})O_3$—$PbTiO_3$ ("PIN-PMN-PT"), Pb(ZrTi) ("PZT"), or the like. According to an embodiment, the acoustic dematching layer 208 may be configured to decrease insertion losses and enhance a frequency bandwidth of the transducer elements 206. For example, the acoustic dematching layer 208 may be tungsten carbide, silicon carbide, or the like. According to an embodiment, the backing layer 210 may be configured to attenuate ultrasound signals directed from the transducer elements 206 in a direction opposite to the subject, and attenuate ultrasound signals deflected by a housing of the ultrasound probe 102. For example, the backing layer 210 may be an epoxy, a metal, or the like.

The number and arrangement of the components of the ultrasound probe 102 shown in FIG. 2 are provided as an example. In practice, the ultrasound probe 102 may include additional components, fewer components, different components, or differently arranged components than those shown in FIG. 2. Additionally, or alternatively, a set of components (e.g., one or more components) of the ultrasound probe 102 may perform one or more functions described as being performed by another set of components of the ultrasound probe 102.

Figure 3:
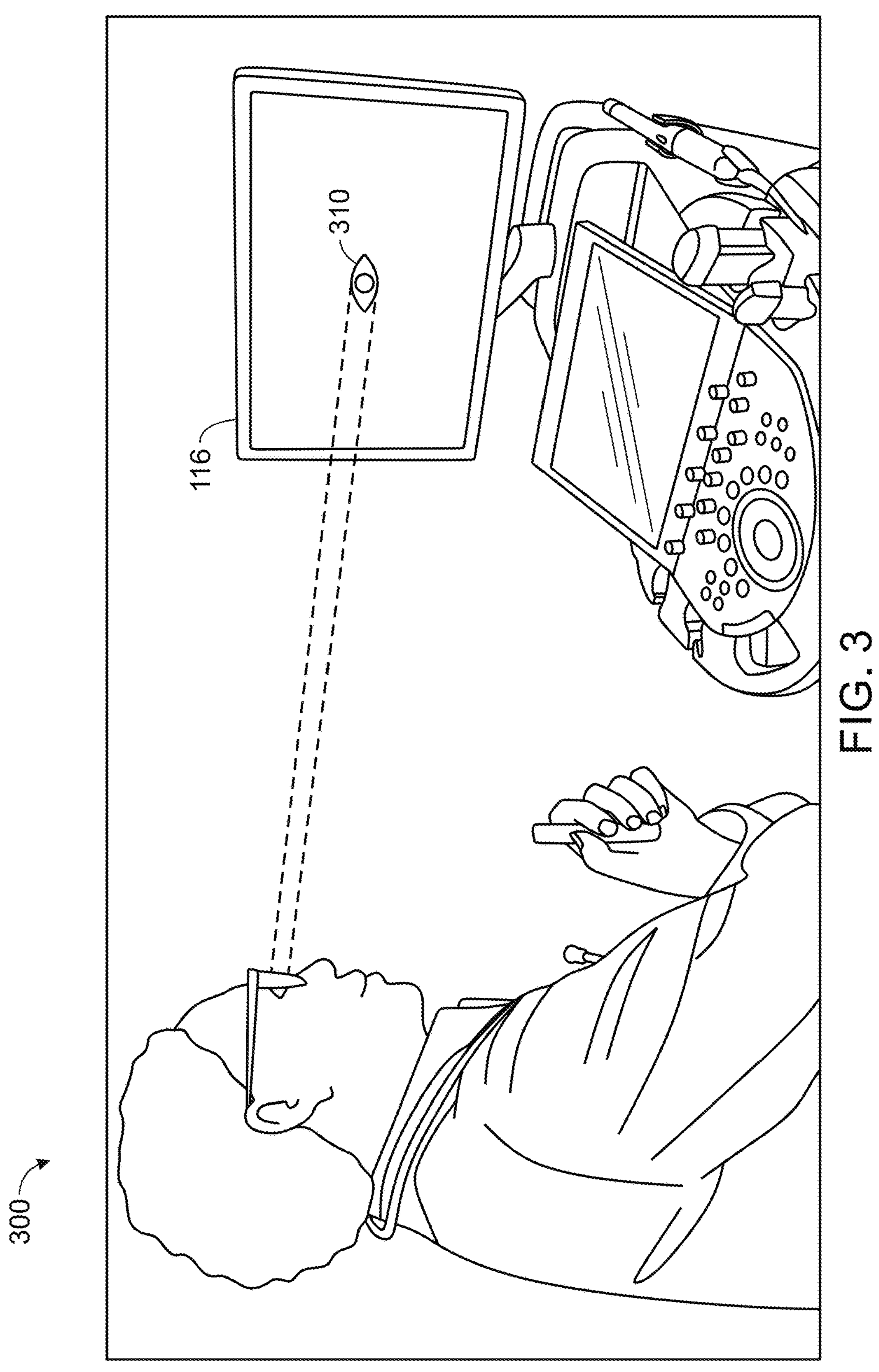
FIG. 3 is a diagram of determining a gaze location of a user on a display of the ultrasound system for displaying ultrasound preview images based on a gaze location of a user.

FIG. 3 is a diagram 300 of determining a gaze location of a user on a display 116 of the ultrasound system 100 for displaying ultrasound preview images based on a gaze location of a user. As shown in FIG. 3, a user (e.g., a clinician, a sonographer, medical personnel, or the like) may view information displayed via the display 116 of the ultrasound system 100. The camera 122 may acquire gaze location information of the user based on the user viewing the display 116 of the ultrasound system 100. For example, the gaze location information may be images of the eyes of the user, images of portions of the eyes of the user, or the like. The ultrasound system 100 may determine a gaze location 310 of the user on the display 116 of the ultrasound system 100 based on the gaze location information acquired by the camera 122. For example, the ultrasound system 100 may determine the gaze location 310 of the user on the display 116 of the ultrasound system 100 based on a position of the eyes, movement of the eyes, size of the eyes, position of the eyes relative to another anatomical feature, or the like. In this way, the ultrasound system 100 may determine a particular location on the display 116 that the user is gazing at. It should be understood that the representation of an eye shown in relation to the gaze location 310 is used for reference herein and might not actually be displayed via the display 116.

Figure 4:
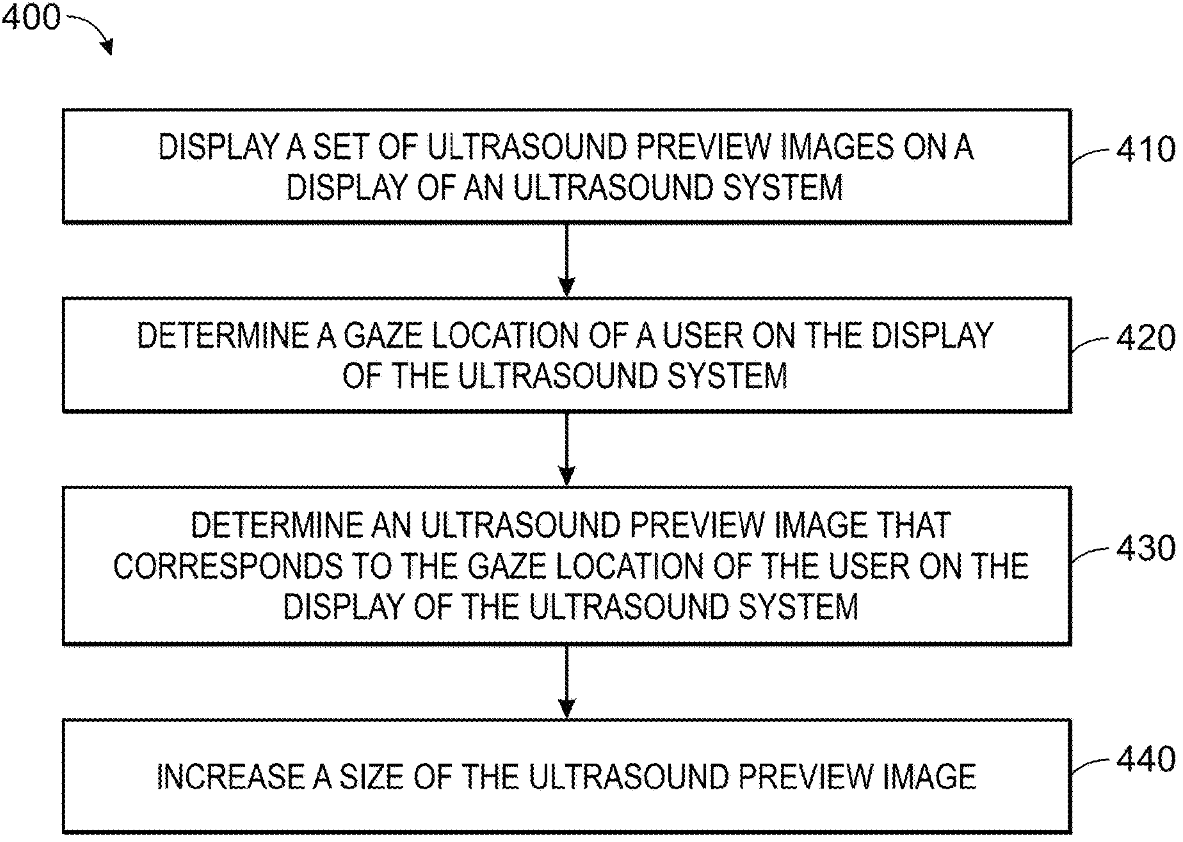
FIG. 4 is a flowchart of an example process for increasing a size of an ultrasound preview image based on a gaze location of a user on a display of an ultrasound system.

FIG. 4 is a flowchart of an example process 400 for increasing a size of an ultrasound preview image based on a gaze location of a user on a display of an ultrasound system. According to an embodiment, the process 400 may be performed by the processor 114. Alternatively, in another embodiment, one or more operations of the process 400 may be performed by another component of the ultrasound system 100, such as the ultrasound probe 102, the transmit beamformer 104, the transmitter 106, the receiver 108, the receive beamformer 110, the user input device 112, the display 116, the memory 118, the communication interface 120, and/or the camera 122.

As shown in FIG. 4, the process 400 may include displaying a set of ultrasound preview images on a display of an ultrasound system (operation 410). For example, the processor 114 may display the set of ultrasound preview images on the display 116 of the ultrasound system 100 to permit the user to view the ultrasound preview images.

According to an embodiment, the set of ultrasound preview images may correspond to a set of ultrasound images stored by, or accessed by, the ultrasound system 100. For example, the set of ultrasound preview images may be smaller size, smaller resolution, etc., versions of the set of ultrasound images.

According to an embodiment, the set of ultrasound preview images may correspond to a particular subject. For example, each of the ultrasound preview images of the set of ultrasound preview images may correspond to a same underlying subject. Additionally, or alternatively, the set of ultrasound preview images may correspond to a particular exam of a particular subject. For example, each of the ultrasound preview images of the set of ultrasound preview images may correspond to a same exam. According to an embodiment, the ultrasound system 100 may display multiple sets of ultrasound preview images. For example, the ultrasound system 100 may display a first set of ultrasound preview images that corresponds to a first exam of a subject, a second set of ultrasound preview images that corresponds to a second exam of a subject, etc. Additionally, or alternatively, the ultrasound system 100 may display a first set of ultrasound preview images that corresponds to a first exam of a first subject, may display a second set of ultrasound preview images that corresponds to a first exam of a second subject, or the like.

According to an embodiment, the ultrasound system 100 may display the set of ultrasound preview images in a display configuration. For example, the display configuration may be a one-dimensional list, an n×n list, an n×m list, or the like. According to an embodiment, the ultrasound system 100 may display a preconfigured number of ultrasound preview images for each set of ultrasound preview images. For example, the ultrasound system 100 may display three ultrasound preview images, five ultrasound preview images, six ultrasound preview images, etc.

According to an embodiment, the ultrasound system 100 may display each ultrasound preview image of the set of ultrasound preview images in a particular size. The size of an ultrasound preview image may be smaller than as compared to a size of the actual ultrasound image to which the ultrasound preview image corresponds. Additionally, or alternatively, the ultrasound system 100 may display each ultrasound preview image of the set of ultrasound preview images in a particular resolution. The resolution of an ultrasound preview image may be reduced as compared to a resolution of the actual ultrasound image to which the ultrasound preview image corresponds. In this way, the ultrasound system 100 may display the set of ultrasound preview images for viewing by the user.

As further shown in FIG. 4, the process 400 may include determining a gaze location of a user on the display of the ultrasound system (operation 420). For example, the processor 114 may determine a gaze location of the user on the display 116 of the ultrasound system 100 based on gaze location information acquired by the camera 122.

As further shown in FIG. 4, the process 400 may include determining an ultrasound preview image that corresponds to the gaze location of the user on the display of the ultrasound system (operation 430). For example, the processor 114 may determine an ultrasound preview image that corresponds to the gaze location of the user on the display 116 of the ultrasound system 100. According to an embodiment, the ultrasound system 100 may determine an ultrasound preview image that overlaps the gaze location of the user. For example, the ultrasound system 100 may determine an ultrasound preview image that entirely overlaps the gaze location of the user. Alternatively, the ultrasound system 100 may determine an ultrasound preview image that partially overlaps the gaze location of the user. In this case, the amount of overlap may be greater than a threshold amount, such as 50%, 60%, 70%, etc.

As further shown in FIG. 4, the process 400 may include increasing a size of the ultrasound preview image (operation 440). For example, the processor 114 may increase a size of the ultrasound preview image that corresponds to the gaze location of the user on the display 116 of the ultrasound system 100.

According to an embodiment, the ultrasound system 100 may increase the size of the ultrasound preview image from an initial size of the ultrasound preview image to a final size. The final size may be a size that is greater than the initial size of the ultrasound preview image. According to an embodiment, the final size may be a size of the ultrasound image to which the ultrasound preview image corresponds. Alternatively, the final size may be an intermediate size that is between the initial size of the ultrasound preview image and the size of the ultrasound image.

According to an embodiment, the ultrasound system 100 may increase the size of the ultrasound preview image from the initial size to the final size in a single step and for a first duration. Alternatively, the ultrasound system 100 may iteratively increase the size of the ultrasound preview image from an initial size of the ultrasound preview image to one or more intermediate sizes, and, ultimately, to the final size of the ultrasound image for a second duration. The second duration may be greater than the first duration. For example, the ultrasound system 100 may increase the size of the ultrasound preview image from an initial size to a first size at a first time point, increase the size of the ultrasound preview image from the first size to a second size at a second time point, etc. The ultrasound system 100 may iteratively increase the size of the ultrasound preview image to a final size. In this way, the ultrasound system 100 may increase the size of the ultrasound preview image to the final size via a gradual animated transition by iteratively increasing the size of the ultrasound preview image.

According to an embodiment, the ultrasound system 100 may increase the size of the ultrasound preview image based on the gaze location of the user corresponding to the ultrasound preview image for a threshold amount of time. For example, the threshold amount of time may be 1 second, 2 seconds, 3 seconds, etc. In this case, the ultrasound system 100 may determine that the gaze location of the user corresponds to the ultrasound preview image for the threshold amount of time, and increase the size of the ultrasound preview image based on determining that the gaze location of the user corresponds to the ultrasound preview image for the threshold amount of time. In the embodiment in which the ultrasound system 100 iteratively increases the size of the ultrasound preview image, the ultrasound system 100 may iteratively determine that the gaze location of the user corresponds to the displayed ultrasound preview image.

According to an embodiment, the ultrasound system 100 may increase a resolution of the ultrasound preview image based on the gaze location of the user corresponding to the ultrasound preview image. For example, the ultrasound system 100 may increase the resolution of the ultrasound preview image from an initial resolution of the ultrasound preview image to a final resolution. The ultrasound system 100 may increase the resolution of the ultrasound preview image in a similar manner as described above with respect to the increase of the size of the ultrasound preview image.

According to an embodiment, the ultrasound system 100 may maintain a display of other ultrasound preview images based on increasing the size of the ultrasound preview image. For example, the ultrasound system 100 may maintain the respective positions of the other ultrasound preview images that do not correspond to the gaze location of the user. Alternatively, the ultrasound system 100 may adjust the respective positions of the other ultrasound preview images that do not correspond to the gaze location of the user based on increasing the size of the ultrasound preview image that does correspond to the gaze location of the user. In this way, the other ultrasound preview images may remain visible during the increasing of the size of the ultrasound preview image so as to not disrupt the search process of the user. Additionally, or alternatively, the ultrasound system 100 may maintain the respective sizes of the other ultrasound preview images that do not correspond to the gaze location of the user.

According to an embodiment, the ultrasound system 100 may adjust a display of other ultrasound preview images based on increasing the size of the ultrasound preview image. For example, the ultrasound system 100 may decrease the size of the other ultrasound preview images that do not correspond to the gaze location of the user. Alternatively, the ultrasound system 100 may increase an opacity of the other ultrasound preview images that do not correspond to the gaze location of the user. Alternatively, the ultrasound system 100 may decrease a resolution of the other ultrasound preview images that do not correspond to the gaze location of the user. Alternatively, the ultrasound system 100 may remove the display of the other ultrasound preview images that do not correspond to the gaze location of the user.

According to an embodiment, the ultrasound system 100 may adjust a display configuration of the set of ultrasound preview images based on increasing the size of the ultrasound preview image. For example, the ultrasound system 100 may adjust a display configuration of the set of ultrasound preview images from a first display configuration (e.g., a one-dimensional list) to a second display configuration (e.g., a two-dimensional list) based on increasing the size of the ultrasound preview image.

According to an embodiment, the ultrasound system 100 may increase the size of another ultrasound preview image that does not correspond to the gaze location of the user based on increasing the size of the ultrasound preview image that does correspond to the gaze location of the user. For example, the ultrasound system 100 may increase the size of another ultrasound preview image that is adjacent to the ultrasound preview image in the list of ultrasound preview images. Additionally, or alternatively, if the ultrasound system 100 adjusts the display configuration of the set of ultrasound preview images from a first display configuration (e.g., a one-dimensional list) to a second display configuration (e.g., a two-dimensional list) based on increasing the size of the ultrasound preview image, then the ultrasound system 100 may increase the size of the other ultrasound preview images that are displayed in the second display configuration. Restated, the ultrasound system 100 may rearrange the display of the ultrasound preview images based on increasing the size of the ultrasound preview image.

Although FIG. 4 depicts particular operations and a particular sequence of operations, it should be understood that other embodiments may include different operations and/or a different sequence of operations.

FIGS. 5A-5D are diagrams of an example process 500 for increasing a size of an ultrasound preview image based on a gaze location of a user on a display of an ultrasound system according to an embodiment.

Figure 5A:
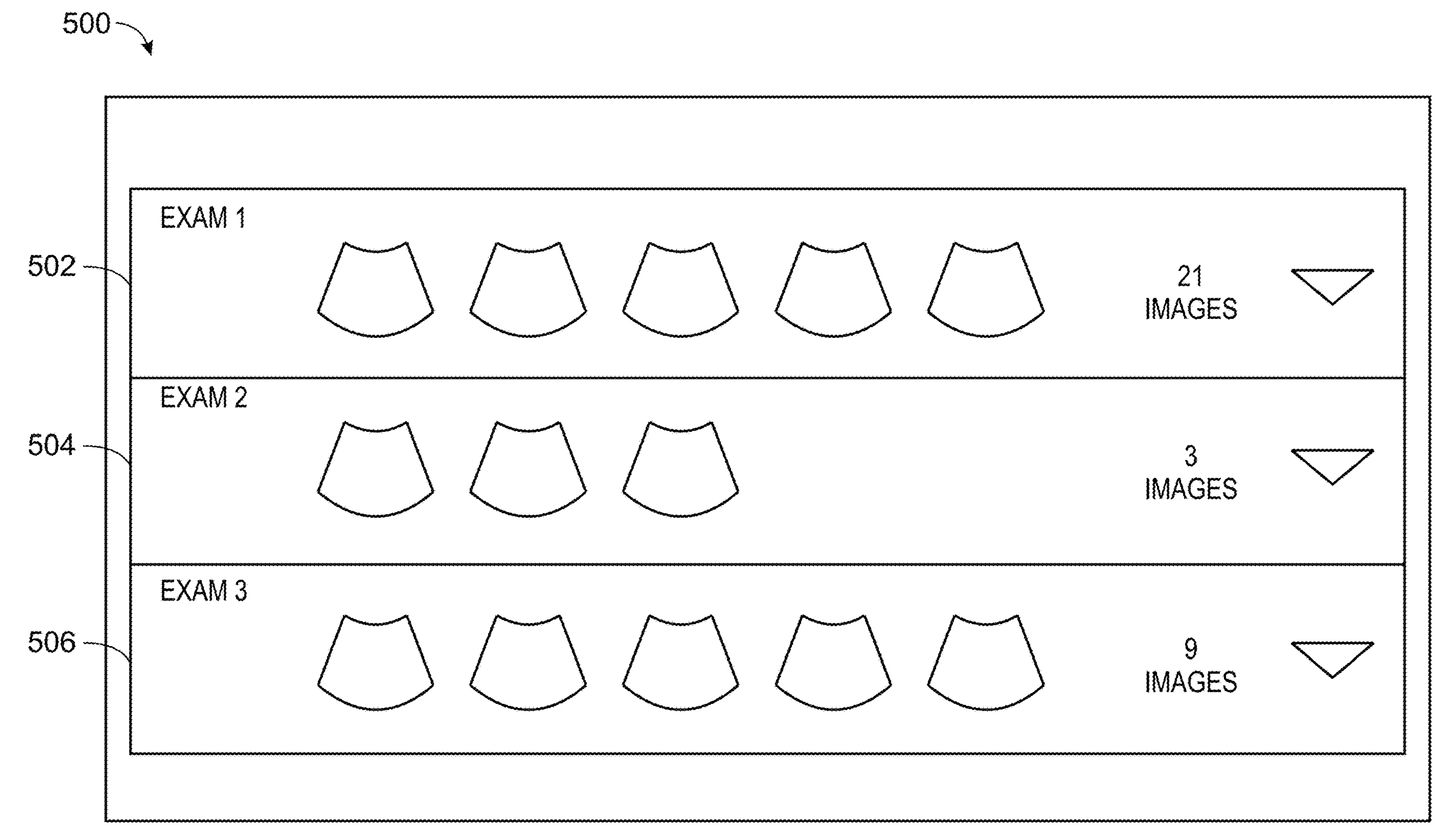
FIGS. 5A-5D are diagrams of an example process for increasing a size of an ultrasound preview image based on a gaze location of a user on a display of an ultrasound system according to an embodiment.

As shown in FIG. 5A, the ultrasound system 100 may display, via the display 116, a first set of ultrasound preview images 502 corresponding to a first exam, may display a second set of ultrasound preview images 504 corresponding to a second exam, and may display a third set of ultrasound preview images 506 corresponding to a third exam. As shown, the first exam may include twenty-one ultrasound images, the second exam may include three images, and the third exam may include nine images. The ultrasound system 100 may display five ultrasound preview images for the first exam, display three ultrasound preview images for the second exam, and display five ultrasound preview images for the third exam. The ultrasound system 100 may display, via the display 116, the first set of ultrasound preview images 502, the second set of ultrasound preview images 504, and the third set of ultrasound preview images 506, respectively, in a display configuration including one-dimensional lists. The ultrasound system 100 may display, via the display 116, each of the ultrasound preview images in a particular size.

Figure 5B:
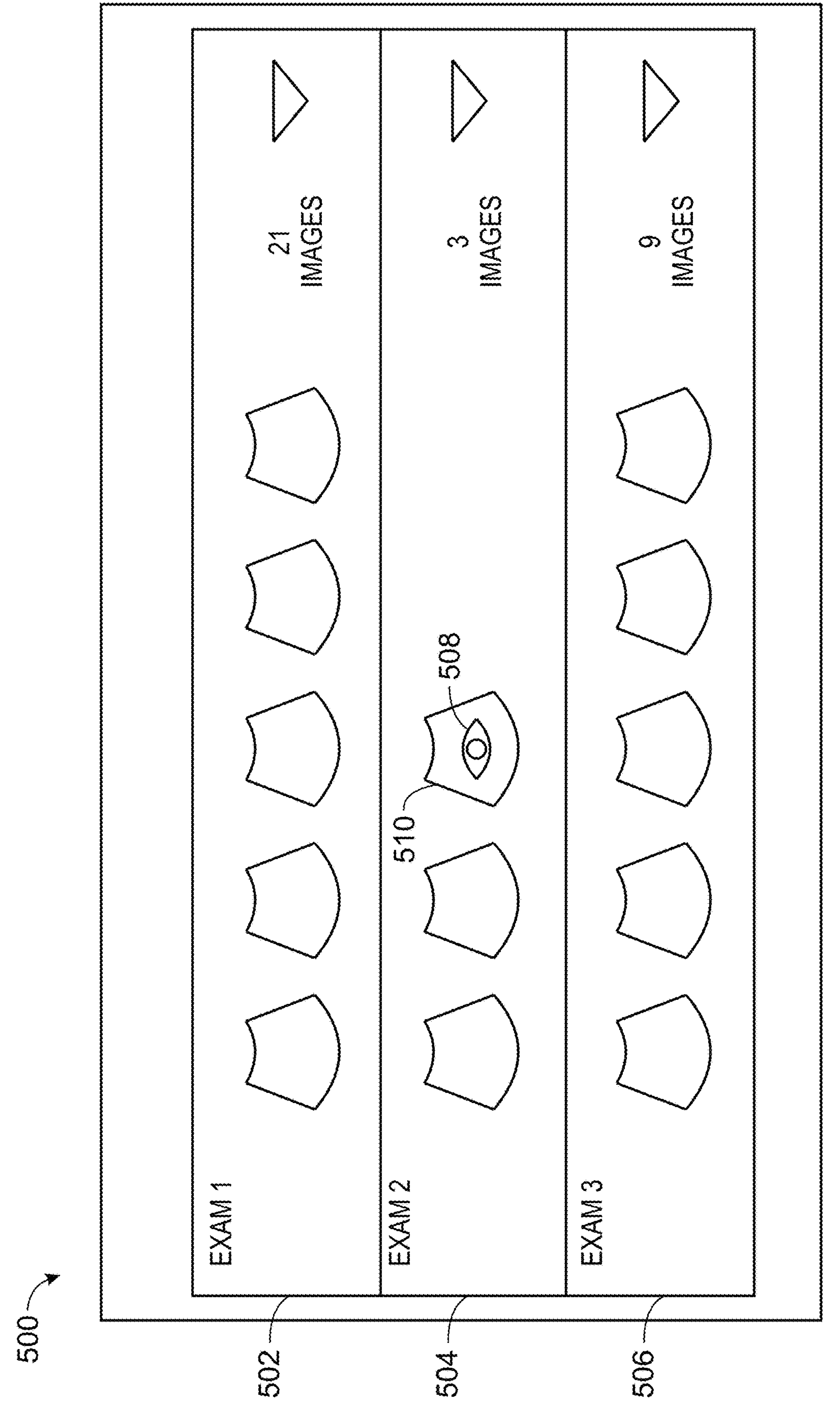

As shown in FIG. 5B, the ultrasound system 100 may determine a gaze location 508 of a user on the display 116 of the ultrasound system 100. For example, the camera 122 may acquire gaze location information, and the ultrasound system 100 may determine the gaze location 508 of the user on the display 116 of the ultrasound system 100 based on the gaze location information. As further shown in FIG. 5B, the ultrasound system 100 may determine an ultrasound preview image 510 that corresponds to the gaze location 508 of the user on the display 116 of the ultrasound system 100. For example, the ultrasound system 100 may determine that the gaze location 508 partially, or entirely, overlaps the ultrasound preview image 510, and determine that the ultrasound preview image 510 corresponds to the gaze location 508 based on determining the overlap.

Figure 5C:
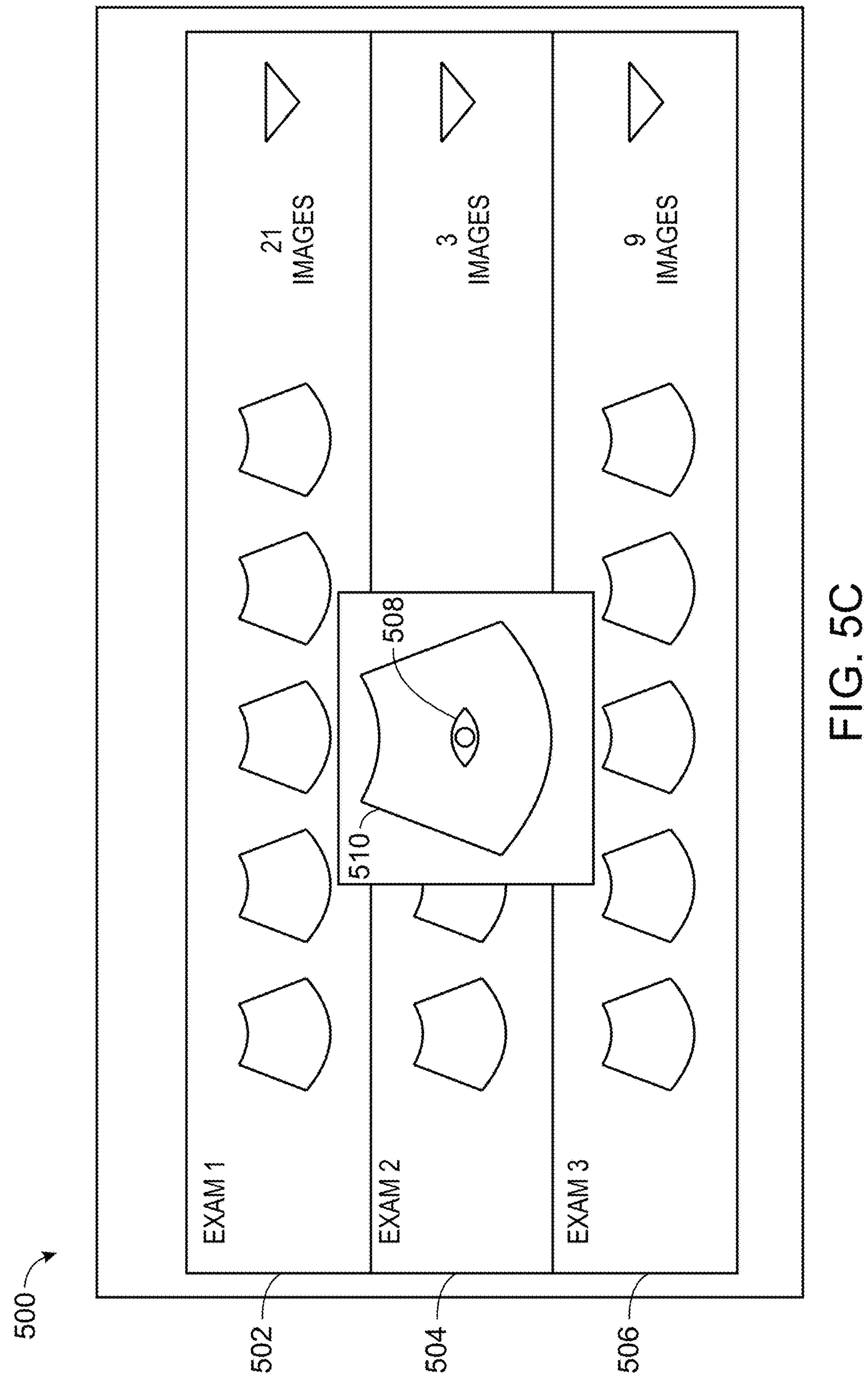
Figure 5D:
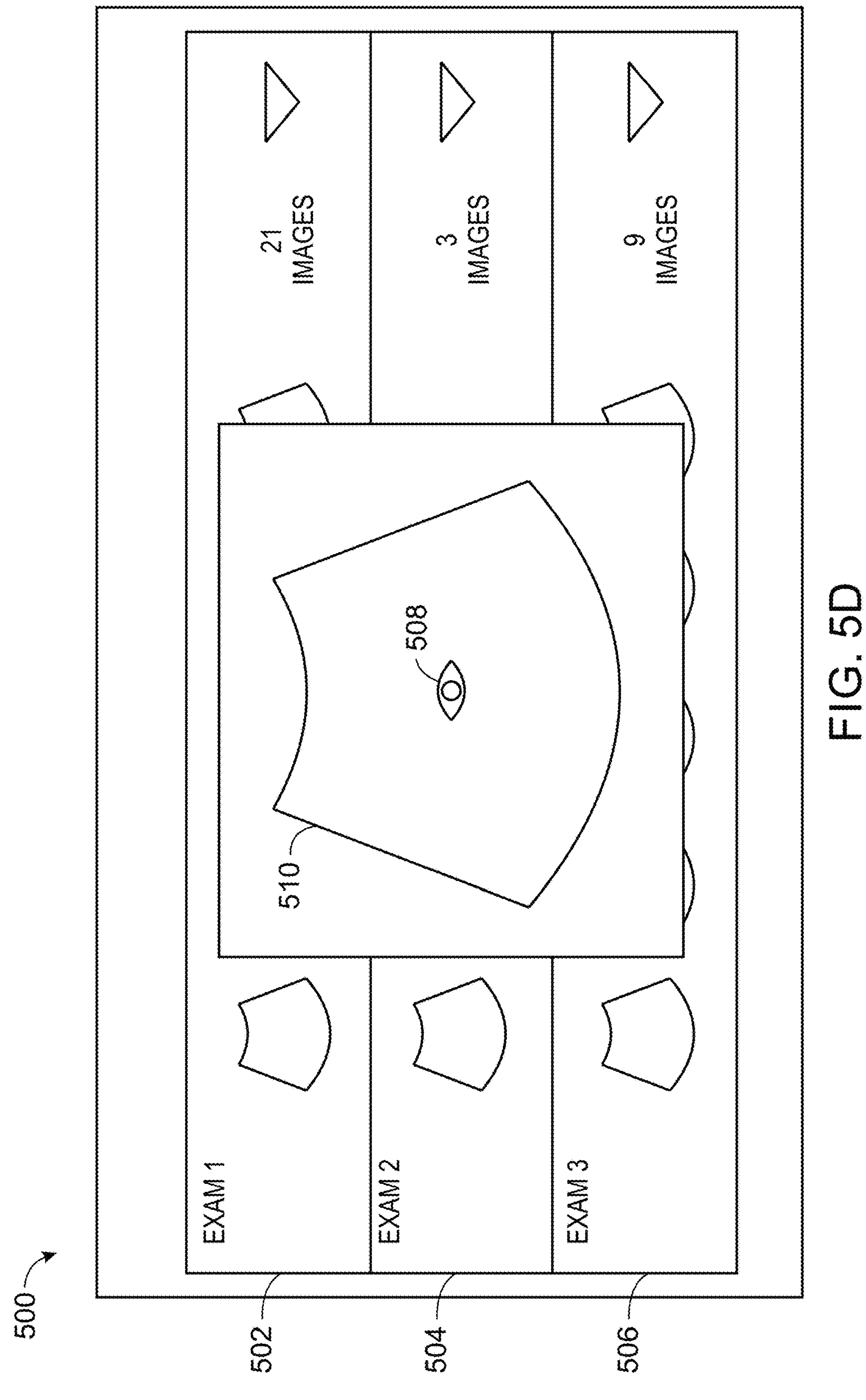

As shown in FIG. 5C, the ultrasound system 100 may increase a size of the ultrasound preview image 510. For example, as shown, the ultrasound system 100 may increase a size of the ultrasound preview image 510 as compared to the size of the ultrasound preview image 510 as shown in FIGS. 5A and 5B. As shown in FIG. 5D, the ultrasound system 100 may further increase a size of the ultrasound preview image 510. For example, as shown, the ultrasound system 100 may increase a size of the ultrasound preview image 510 as compared to the size of the ultrasound preview image 510 as shown in FIGS. 5A, 5B, and 5C.

In this way, the ultrasound system 100 may increase a size of the ultrasound preview image 510 based on the user merely viewing the ultrasound preview image 510. Restated, the user might not be required to physically, or manually, interact with the user input device 112 of the ultrasound system 100 in order to increase the size of the ultrasound preview image 510.

FIGS. 6A-6D are diagrams of an example process 600 for increasing a size of an ultrasound preview image based on a gaze location of a user on a display of an ultrasound system according to another embodiment.

Figure 6A:
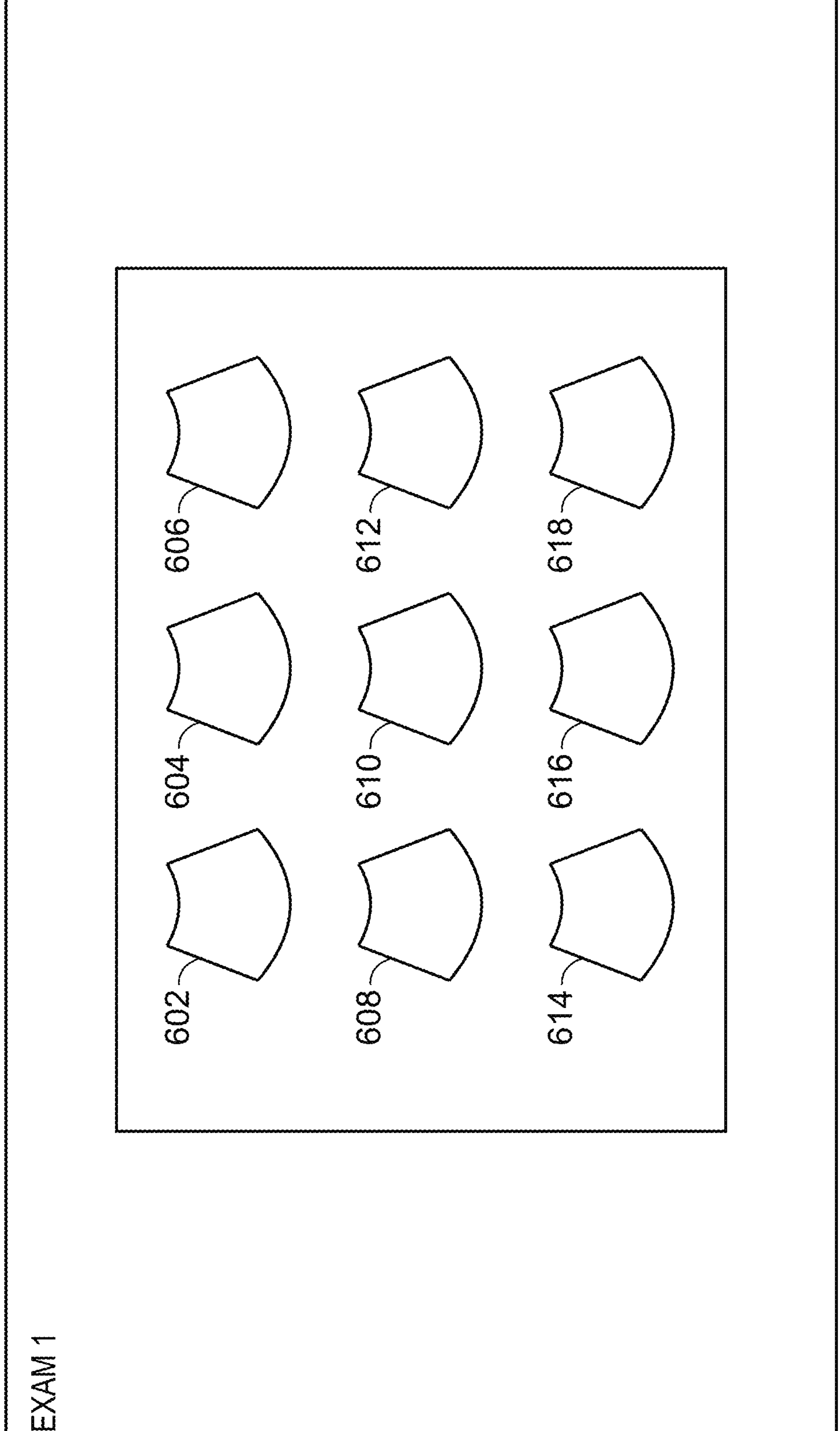
FIGS. 6A-6D are diagrams of an example process for increasing a size of an ultrasound preview image based on a gaze location of a user on a display of an ultrasound system according to another embodiment.

As shown in FIG. 6A, the ultrasound system 100 may display, via the display 116, a set of ultrasound preview images corresponding to an exam. For example, as shown, the ultrasound system 100 may display, via the display 116, a first ultrasound preview image 602, a second ultrasound preview image 604, a third ultrasound preview image 606, a fourth ultrasound preview image 608, a fifth ultrasound preview image 610, a sixth ultrasound preview image 612, a seventh ultrasound preview image 614, an eighth ultrasound preview image 616, and a ninth ultrasound preview image 618. The ultrasound system 100 may display, via the display 116, the set of ultrasound preview images in a display configuration including a 3×3 list. The ultrasound system 100 may display, via the display 116, each of the ultrasound preview images in a particular size.

Figure 6B:
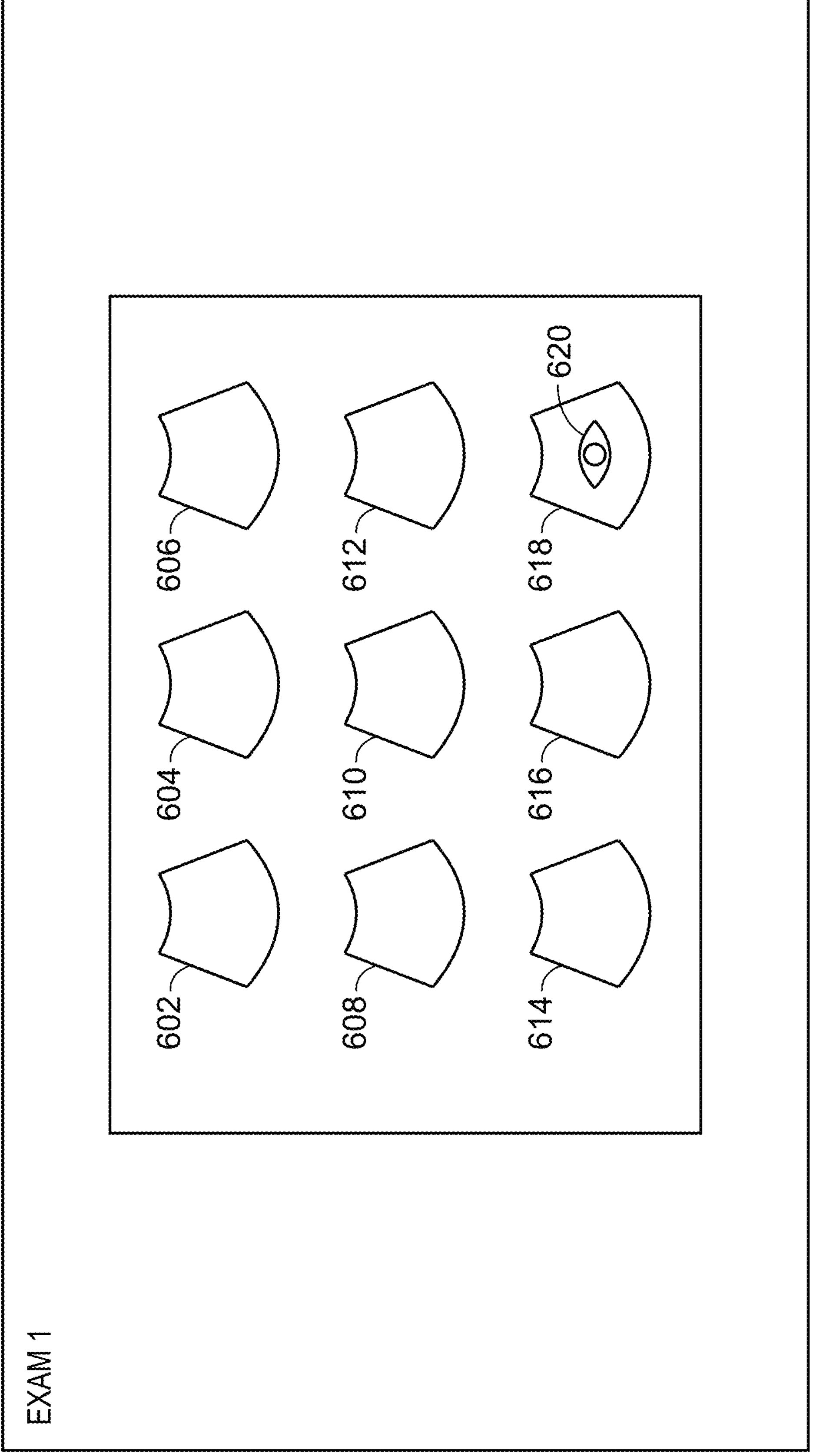

As shown in FIG. 6B, the ultrasound system 100 may determine a gaze location 620 of a user on the display 116 of the ultrasound system 100. For example, the camera 122 may acquire gaze location information, and the ultrasound system 100 may determine the gaze location 620 of the user on the display 116 of the ultrasound system 100 based on the gaze location information. As further shown in FIG. 6B, the ultrasound system 100 may determine the ninth ultrasound preview image 618 that corresponds to the gaze location 620 of the user on the display 116 of the ultrasound system 100. For example, the ultrasound system 100 may determine that the gaze location 620 partially, or entirely, overlaps the ninth ultrasound preview image 618, and determine that the ninth ultrasound preview image 618 corresponds to the gaze location 620 based on determining the overlap.

Figure 6C:
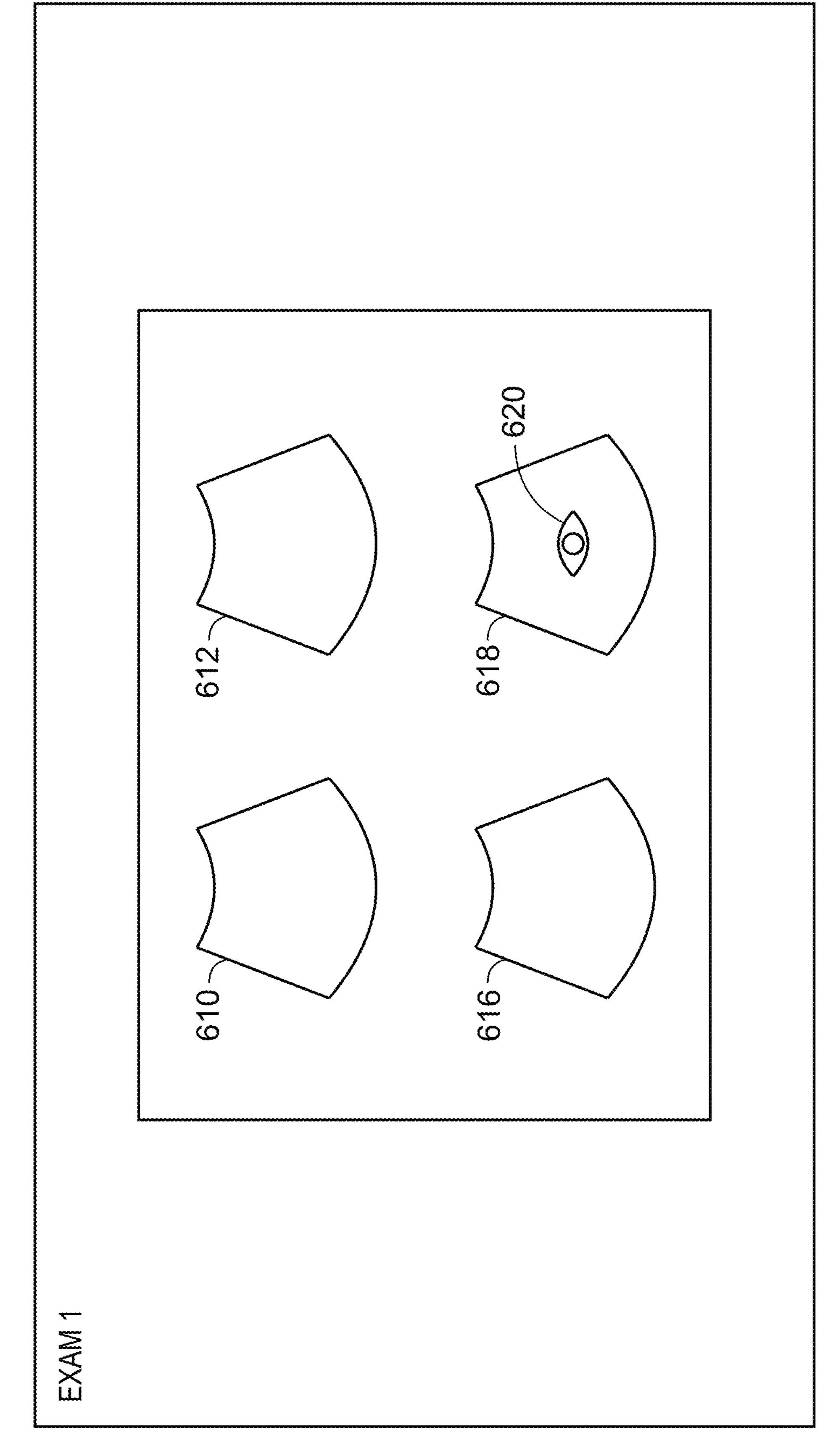

As shown in FIG. 6C, the ultrasound system 100 may increase a size of the ultrasound preview image 618. For example, as shown, the ultrasound system 100 may increase a size of the ultrasound preview image 618 as compared to the size of the ultrasound preview image 618 as shown in FIGS. 6A and 6B. Further, as shown in FIG. 6C, the ultrasound system 100 may adjust the display configuration of the 3×3 list into a display configuration of a 2×2 list. Based on the adjusted display configuration, the ultrasound system 100 may display the fifth ultrasound preview image 610, the sixth ultrasound preview image 612, the eighth ultrasound preview image 616, and the ninth ultrasound preview image 618. Further, each of the respective sizes of the fifth ultrasound preview image 610, the sixth ultrasound preview image 612, the eighth ultrasound preview image 616, and the ninth ultrasound preview image 618 may be greater than as compared to the sizes as shown in FIGS. 6A and 6B.

Figure 6D:
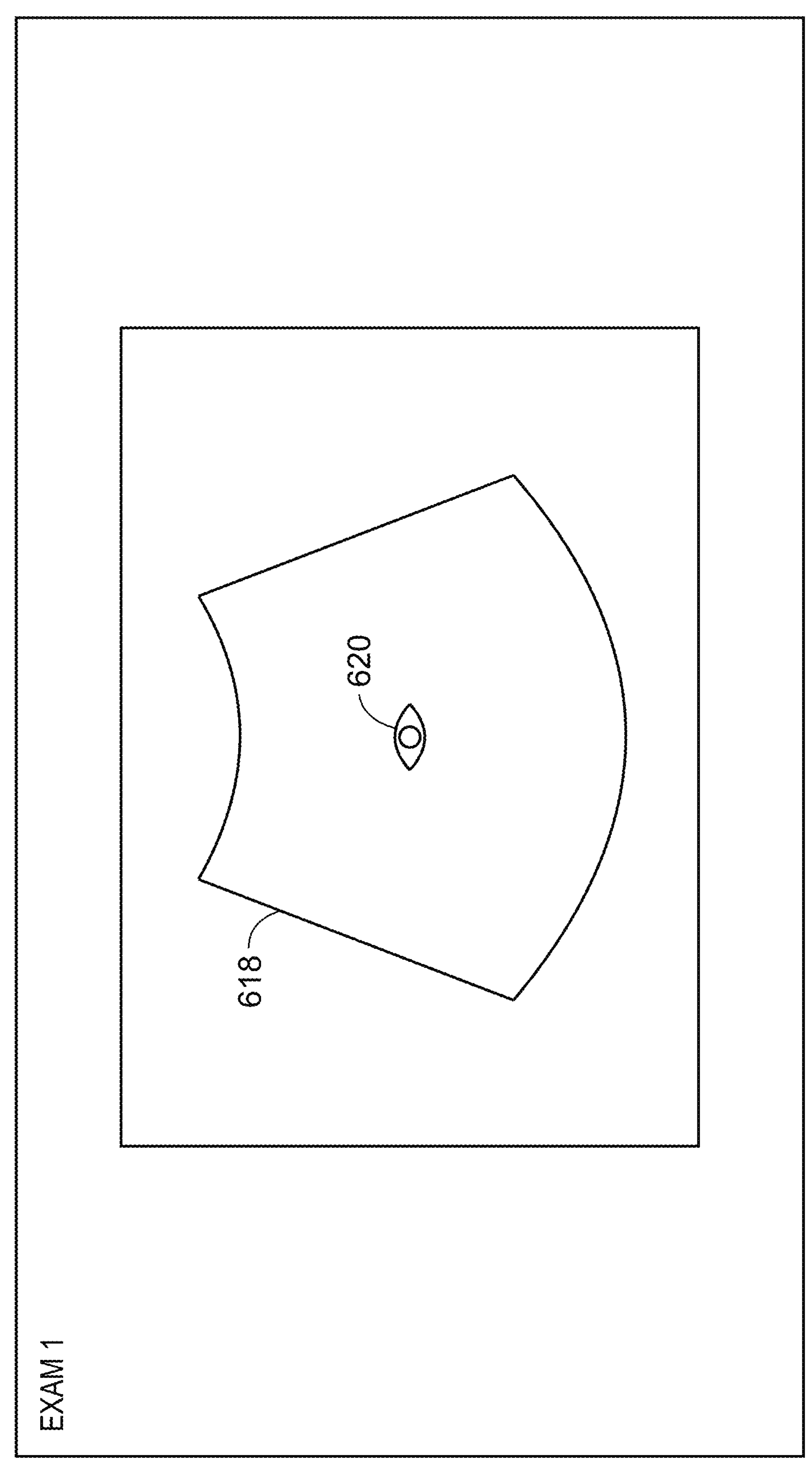

As shown in FIG. 6D, the ultrasound system 100 may further increase a size of the ninth ultrasound preview image 618. For example, as shown, the ultrasound system 100 may increase a size of the ninth ultrasound preview image 618 as compared to the size of the ninth ultrasound preview image 618 as shown in FIGS. 6A, 6B, and 6C. Further, as shown in FIG. 6D, the ultrasound system 100 may adjust the display configuration of the 3×3 list into a display configuration of a single ultrasound preview image. Based on the adjusted display configuration, the ultrasound system 100 may only display the ninth ultrasound preview image 618.

In this way, the ultrasound system 100 may increase a size of the ninth ultrasound preview image 618 based on the user merely viewing the ninth ultrasound preview image 618. Restated, the user might not be required to physically, or manually, interact with the user input device 112 of the ultrasound system 100 in order to increase the size of the ninth ultrasound preview image 618.

Figure 7:
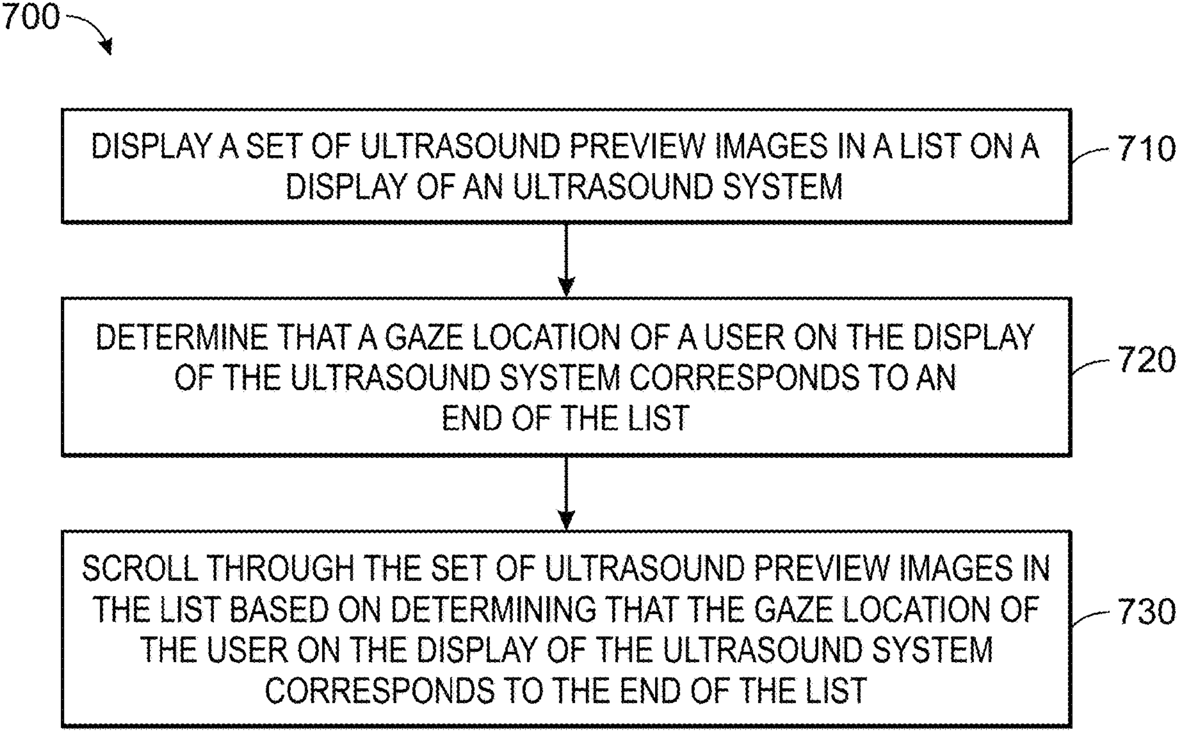
FIG. 7 is a flowchart of an example process for scrolling through a set of ultrasound preview images in a list based on a gaze location of a user on a display of an ultrasound system.

FIG. 7 is a flowchart of an example process 700 for scrolling through a set of ultrasound preview images in a list based on a gaze location of a user on a display of an ultrasound system. According to an embodiment, the process 700 may be performed by the processor 114. Alternatively, in another embodiment, one or more operations of the process 700 may be performed by another component of the ultrasound system 100, such as the ultrasound probe 102, the transmit beamformer 104, the transmitter 106, the receiver 108, the receive beamformer 110, the user input device 112, the display 116, the memory 118, the communication interface 120, and/or the camera 122.

As shown in FIG. 7, the process 700 may include displaying a set of ultrasound preview images in a list on a display of an ultrasound system (operation 710). For example, the processor 114 may display a set of ultrasound preview images in a list on the display 116 of the ultrasound system 100. The ultrasound system 100 may display the set of ultrasound preview images in the list on the display 116 of the ultrasound system 100 in a similar manner as described above in connection with operation 410 of FIG. 4.

As further shown in FIG. 7, the process 700 may include determining that a gaze location of a user on the display of the ultrasound system corresponds to an end of the list (operation 720). For example, the processor 114 may determine that a gaze location of the user on the display of the ultrasound system corresponds to an end of the list. The ultrasound system 100 may determine a gaze location of the user on the display 116 of the ultrasound system 100 based on gaze location information acquired by the camera 122, and determine that the gaze location of the user on the display 116 of the ultrasound system 100 corresponds to an end of the list. The end of the list may be a portion of the list that indicates an end of the displayed ultrasound preview images. For example, the end of the list may be a border of the list, a portion located to the side of the last displayed ultrasound preview image, a portion located below one or more last displayed ultrasound preview images, a portion located above one or more first displayed ultrasound preview images, a particular user interface element that signifies an end of the displayed ultrasound preview images, or the like.

As further shown in FIG. 7, the process 700 may include scrolling through the set of ultrasound preview images based on determining that the gaze location of the user on the display of the ultrasound system corresponds to the end of the list (operation 730). For example, the processor 114 may scroll through the set of ultrasound preview images based on determining that the gaze location of the user on the display 116 of the ultrasound system 100 corresponds to the end of the list.

According to an embodiment, the ultrasound system 100 may scroll through the list based on the display configuration. For example, if the list is a one-dimensional list, the ultrasound system 100 may scroll to the right through the list and/or may scroll through the left through the list. As another example, if the list is two-dimensional list, then the ultrasound system 100 may scroll to the left through the list, scroll to the right through the list, scroll downwards through the list, scroll upwards through the list, etc. Alternatively, the ultrasound system 10 may scroll through the list by updating a display of displayed ultrasound preview images. For example, the ultrasound system 100 may remove one or more displayed ultrasound preview images, and display one or more new ultrasound preview images in the locations of the removed ultrasound preview images.

According to an embodiment, the ultrasound system 100 may scroll through the set of ultrasound preview using a predetermined scroll speed. Additionally, or alternatively, the ultrasound system 100 may determine a scroll speed, and scroll through the set of ultrasound preview images using the determined scroll speed. For example, the ultrasound system 100 may determine the scroll speed based on a duration of which the gaze location of the user has coincided with the end of the list, based on a particular location of the gaze location on the display 116, based on a number of ultrasound preview images that are stored by the ultrasound system 100 and that have yet to be displayed, based on a location in the list, based on a size of the displayed ultrasound preview images, based on a lack of movement of the gaze location, or the like.

Although FIG. 7 depicts particular operations and a particular sequence of operations, it should be understood that other embodiments may include different operations and/or a different sequence of operations.

Figure 8A:
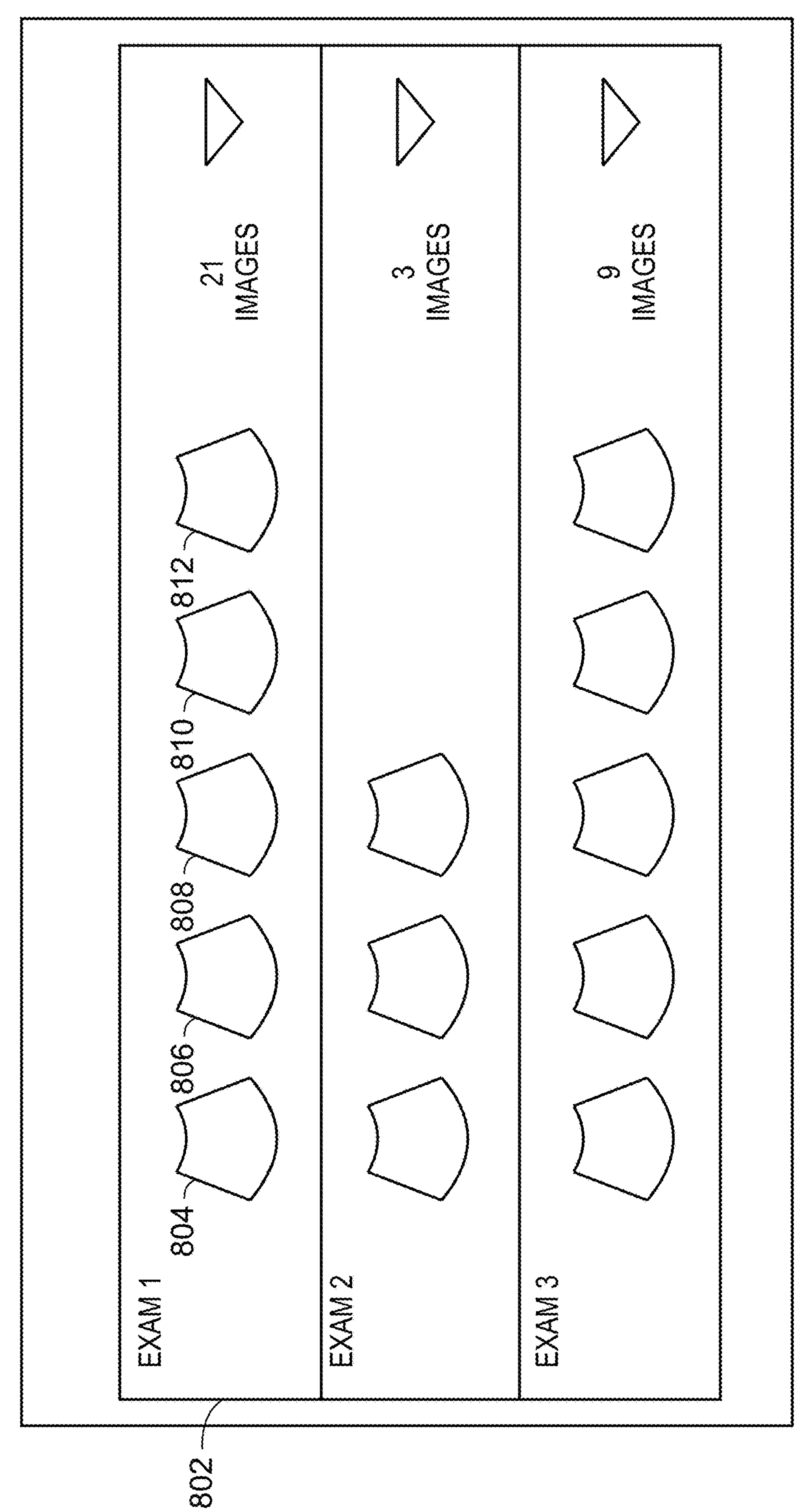
FIGS. 8A-8C are diagrams of an example process for scrolling through a set of ultrasound preview images in a list based on a gaze location of a user on a display of an ultrasound system.
Figure 8B:
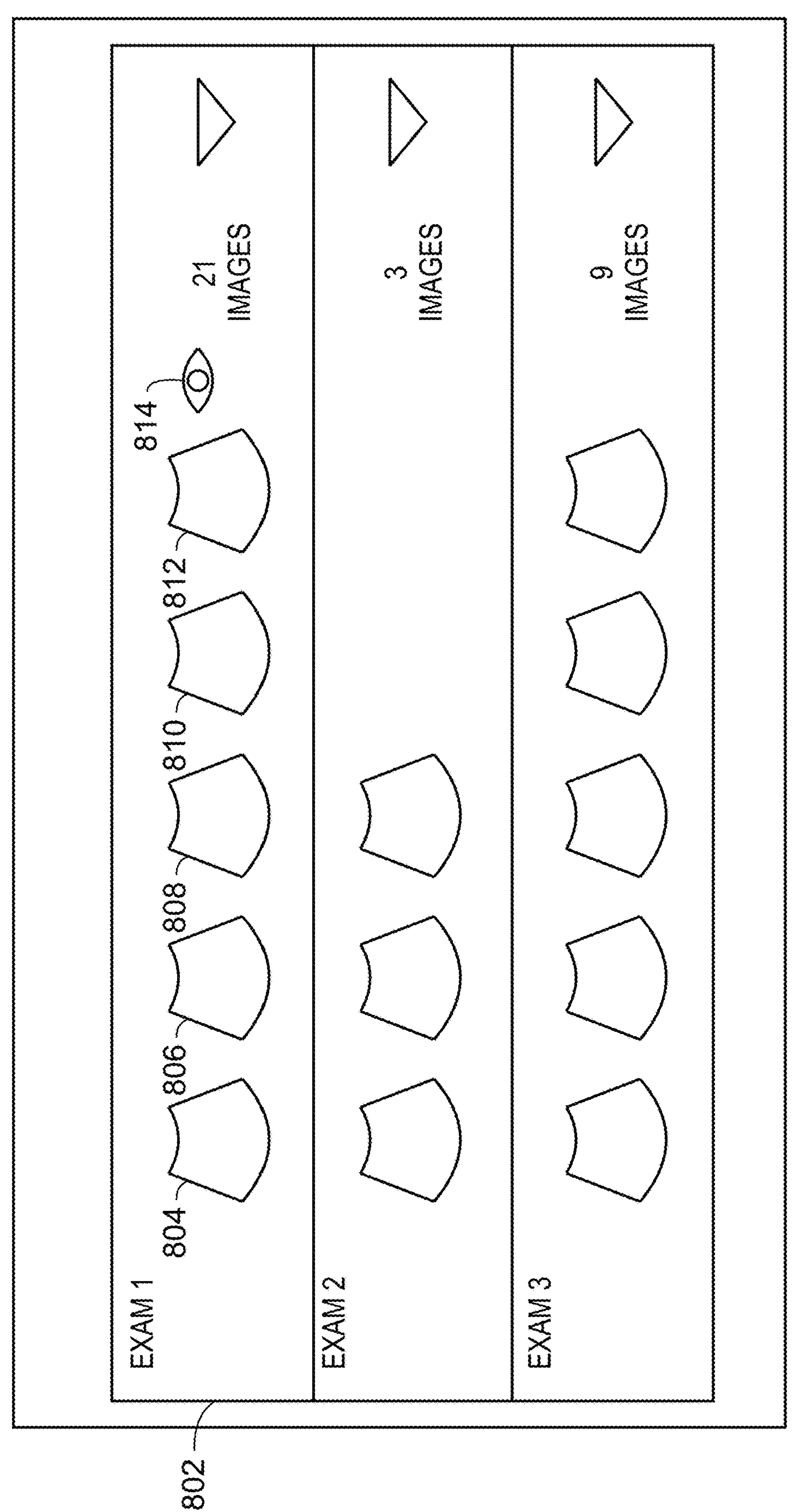
Figure 8C:
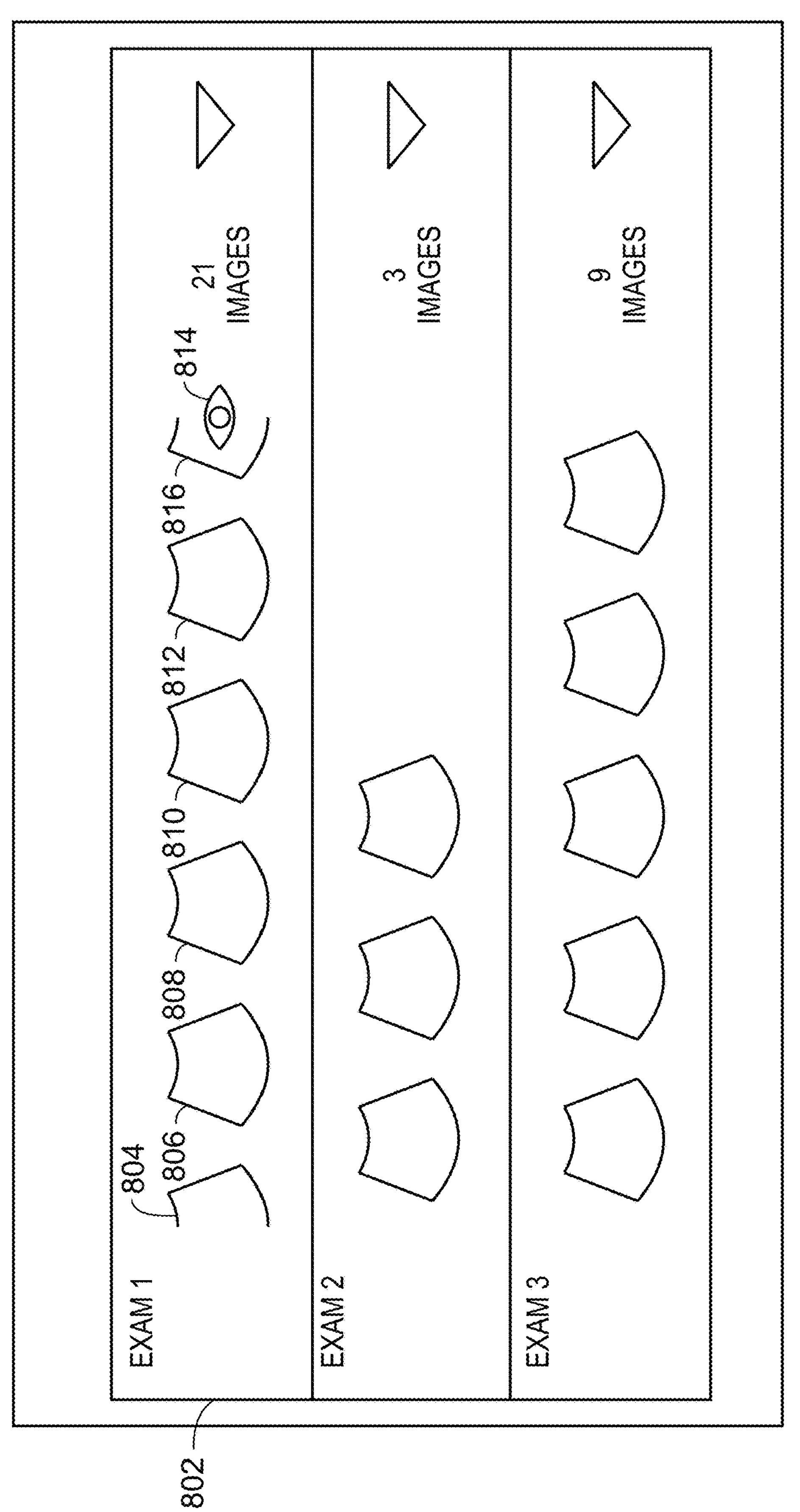

FIGS. 8A-8C are diagrams of an example process for scrolling through a set of ultrasound preview images in a list based on a gaze location of a user on a display of an ultrasound system.

As shown in FIG. 8A, the ultrasound system 100 may display, via the display 116, a first set of ultrasound preview images 802 corresponding to a first exam in a list on the display of the ultrasound system 100, may display a second set of ultrasound preview images corresponding to a second exam in a list on the display of the ultrasound system 100, and may display a third set of ultrasound preview images corresponding to a third exam in a list on the display of the ultrasound system 100. As shown, the first exam may include twenty-one ultrasound images, the second exam may include three images, and the third exam may include nine images. The ultrasound system 100 may display five ultrasound preview images for the first exam in a list on the display of the ultrasound system 100, display three ultrasound preview images for the second exam in a list on the display of the ultrasound system 100, and display five ultrasound preview images for the third exam in a list on the display of the ultrasound system 100. The ultrasound system 100 may display, via the display 116, the first set of ultrasound preview images 802, the second set of ultrasound preview images, and the third set of ultrasound preview images, respectively, in a display configuration including one-dimensional lists. The first set of ultrasound preview images 802 may include a first ultrasound preview image 804, a second ultrasound preview image 806, a third ultrasound preview image 808, a fourth ultrasound preview image 810, and a fifth ultrasound preview image 812 displayed in a list on the display of the ultrasound system 100.

As shown in FIG. 8B, the ultrasound system 100 may determine that a gaze location 814 of a user on the display 116 of the ultrasound system 100 corresponds to an end of the list. For example, the camera 122 may acquire gaze location information, and the ultrasound system 100 may determine the gaze location 814 of the user on the display 116 of the ultrasound system 100 based on the gaze location information. As further shown in FIG. 8B, the ultrasound system 100 may determine that the gaze location 814 of a user on the display 116 of the ultrasound system 100 corresponds to an end of the list of the first set of ultrasound preview images 802. For example, the ultrasound system 100 may determine that the gaze location 814 partially, or entirely, overlaps an end portion of the list of the first set of ultrasound preview images 802.

As shown in FIG. 8C, the ultrasound system 100 may scroll through the first set of ultrasound preview images 802 based on determining that the gaze location 814 of the user on the display 116 of the ultrasound system 100 corresponds to the end of the list. For example, as shown, the ultrasound system 100 may update the display by scrolling through the first set of ultrasound preview images 802. In this case, the first ultrasound preview image 804 may become less visible as the first ultrasound preview image 804 moves towards the left side of the screen, the second ultrasound preview image 806 may move towards the left side of the screen, the third ultrasound preview image 808 may move towards the left side of the screen, the fourth ultrasound preview image 810 may move towards the left side of the screen, the fifth ultrasound preview image 812 may move towards the left side of the screen, and a sixth ultrasound preview image 814 may become visible and enter the list of the first set of ultrasound preview images 502.

In this way, the ultrasound system 100 may scroll through the first set of ultrasound preview images 802 based on the user merely viewing an end of the list of the first set of ultrasound preview images 802. Restated, the user might not be required to physically, or manually, interact with the user input device 112 of the ultrasound system 100 in order to scroll through the first set of ultrasound preview images 802.

Figure 9:
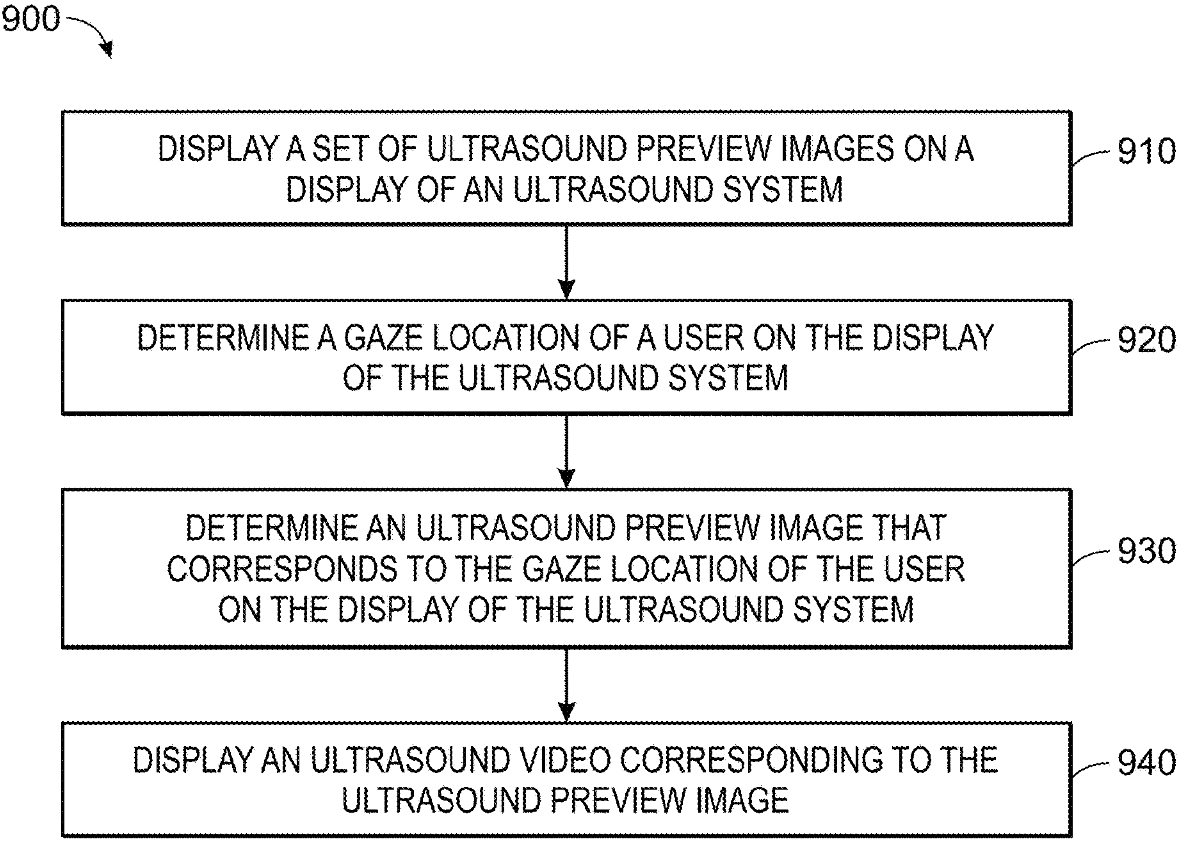
FIG. 9 is a flowchart of an example process for displaying an ultrasound video corresponding to an ultrasound preview image based on a gaze location of a user on a display of an ultrasound system.

FIG. 9 is a flowchart of an example process 900 for displaying an ultrasound video corresponding to an ultrasound preview image based on a gaze location of a user on a display of an ultrasound system. According to an embodiment, the process 900 may be performed by the processor 114. Alternatively, in another embodiment, one or more operations of the process 900 may be performed by another component of the ultrasound system 100, such as the ultrasound probe 102, the transmit beamformer 104, the transmitter 106, the receiver 108, the receive beamformer 110, the user input device 112, the display 116, the memory 118, the communication interface 120, and/or the camera 122.

As shown in FIG. 9, the process 900 may include displaying a set of ultrasound preview images on a display of an ultrasound system (operation 910). For example, the processor 114 may display a set of ultrasound preview images on the display 116 of the ultrasound system 100. The ultrasound system 100 may display the set of ultrasound preview images on the display 116 of the ultrasound system 100 in a similar manner as described above in connection with operation 410 of FIG. 4.

As further shown in FIG. 9, the process 900 may include determining a gaze location of a user on the display of the ultrasound system (operation 920). For example, the processor 114 may determine a gaze location of the user on the display 116 of the ultrasound system 100 in a similar manner as described above in connection with operation 420 of FIG. 4.

As further shown in FIG. 9, the process 900 may include determining an ultrasound preview image that corresponds to the gaze location of the user on the display of the ultrasound system (operation 930). For example, the processor 114 may determine an ultrasound preview image that corresponds to the gaze location of the user on the display 116 of the ultrasound system 100 in a similar manner as described above in connection with operation 430 of FIG. 4.

As further shown in FIG. 9, the process 900 may include displaying an ultrasound video that corresponds to the ultrasound preview image (operation 940). For example, the processor 114 may display an ultrasound video that corresponds to the ultrasound preview image. The ultrasound video may be a video corresponding to the ultrasound preview image. For example, the ultrasound video may be a sequence of ultrasound images corresponding to a particular exam of a subject. According to an embodiment, the ultrasound system 100 may display the ultrasound video based on displaying the ultrasound preview image in a final size. For example, the ultrasound system 100 may increase a size of the ultrasound preview image in a similar manner as described above in connection with FIG. 4 until the ultrasound preview image reaches a final size. Based on the ultrasound preview image being displayed in a final size, the ultrasound system 100 may begin playback of the ultrasound video that corresponds to the ultrasound preview image.

Although FIG. 9 depicts particular operations and a particular sequence of operations, it should be understood that other embodiments may include different operations and/or a different sequence of operations.

Figure 10A:
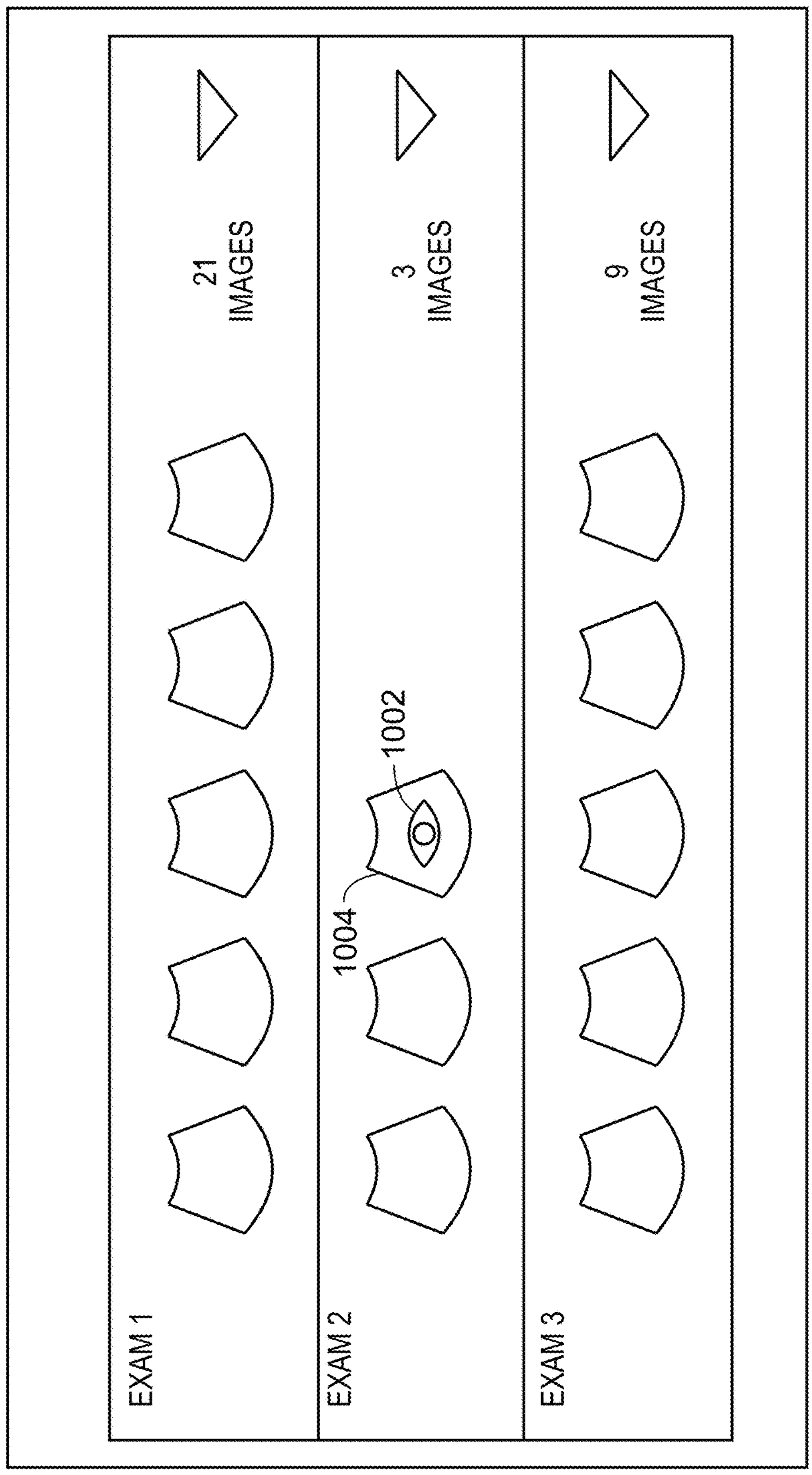
FIGS. 10A and 10B are diagrams of an example process for displaying an ultrasound video corresponding to an ultrasound preview image based on a gaze location of a user on a display of an ultrasound system.
Figure 10B:
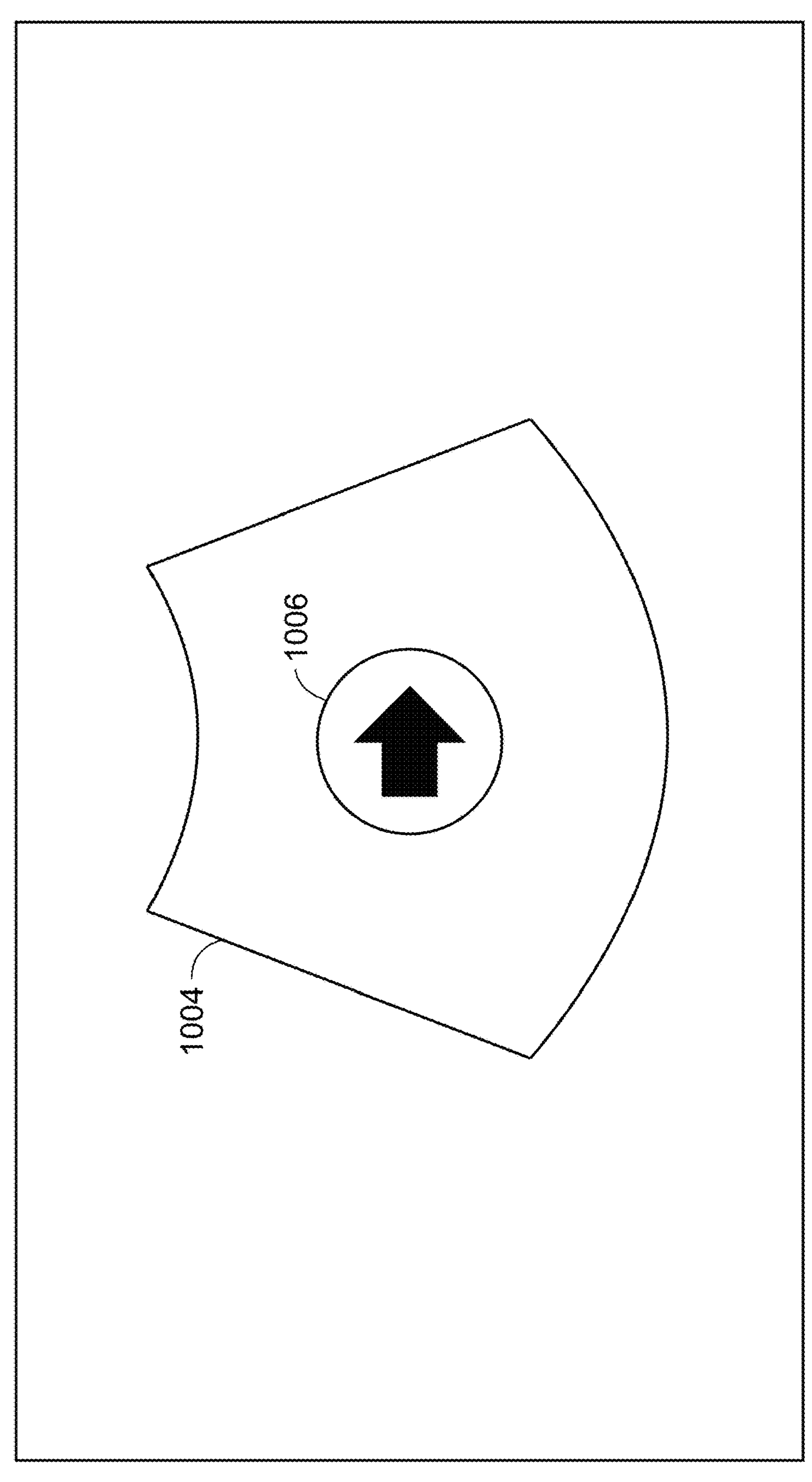

FIGS. 10A and 10B are diagrams of an example process for displaying an ultrasound video corresponding to an ultrasound preview image based on a gaze location of a user on a display of an ultrasound system.

As shown in FIG. 10A, the ultrasound system 100 may display, via the display 116, a first set of ultrasound preview images corresponding to a first exam, may display a second set of ultrasound preview images corresponding to a second exam, and may display a third set of ultrasound preview images corresponding to a third exam. As further shown in FIG. 5A, the ultrasound system 100 may determine a gaze location 1002 of a user on the display 116 of the ultrasound system 100. For example, the camera 122 may acquire gaze location information, and the ultrasound system 100 may determine the gaze location 1002 of the user on the display 116 of the ultrasound system 100 based on the gaze location information. As further shown in FIG. 10A, the ultrasound system 100 may determine an ultrasound preview image 1004 that corresponds to the gaze location 1002 of the user on the display 116 of the ultrasound system 100. For example, the ultrasound system 100 may determine that the gaze location 1002 partially, or entirely, overlaps the ultrasound preview image 1004, and determine that the ultrasound preview image 1004 corresponds to the gaze location 1002 based on determining the overlap. As shown in FIG. 10B, the ultrasound system 100 may display an ultrasound video 1006 that corresponds to the ultrasound preview image 1004. For example, as shown, the ultrasound system 100 may display an ultrasound video 1006 that corresponds to the ultrasound preview image 1004.

In this way, the ultrasound system 100 may display an ultrasound video 1006 that corresponds to the ultrasound preview image 1004 based on the user merely viewing the ultrasound preview image 1004. Restated, the user might not be required to physically, or manually, interact with the user input device 112 of the ultrasound system 100 in order to display an ultrasound video 1006 that corresponds to the ultrasound preview image 1004.

According to other embodiments, the ultrasound system 100 may perform an action based on a gaze location of the user on the display 116 of the ultrasound system 100. For example, the gaze location of the user may coincide with a user interface element. In this case, the ultrasound system 100 may perform an action associated with the user interface element. As examples, the ultrasound system 100 may open a drop-down menu, remove a displayed ultrasound image, open a file, zoom-in, zoom-out, increase resolution, increase size, play an ultrasound video, stop playback of an ultrasound video, change a viewing mode, or the like.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. An ultrasound system comprising:

a memory configured to store instructions; and one or more processors configured to execute the instructions to:

display a plurality of ultrasound preview images that correspond to one or more previous exams of a subject on a display of the ultrasound system;

determine a gaze location of a user on the display of the ultrasound system;

determine an ultrasound preview image, from among the plurality of ultrasound preview images, that corresponds to the gaze location of the user on the display of the ultrasound system; and increase a size of the ultrasound preview image based on determining the ultrasound preview image that corresponds to the gaze location of the user on the display of the ultrasound system.

2. The system of claim 1, wherein the one or more processors are further configured to execute the instructions to:

determine that another gaze location of the user on the display of the ultrasound system corresponds to an end of a list of the plurality of ultrasound preview images; and scroll through the list of the plurality of ultrasound preview images based on determining that the other gaze location of the user on the display of the ultrasound system corresponds to the end of the list of the plurality of ultrasound preview images.

3. The system of claim 1, wherein the one or more processors are further configured to execute the instructions to:

begin playback of an ultrasound video corresponding to the ultrasound preview image based on displaying the ultrasound preview image in a final size.

4. The system of claim 1, wherein the one or more processors are further configured to execute the instructions to:

maintain positions of other ultrasound preview images that do not correspond to the gaze location of the user.

5. The system of claim 1, wherein the one or more processors are further configured to execute the instructions to:

decrease sizes of other ultrasound preview ultrasound images that do not correspond to the gaze location of the user.

6. The system of claim 1, wherein the one or more processors are further configured to execute the instructions to:

remove a display of other ultrasound preview ultrasound images that do not correspond to the gaze location of the user.

7. The system of claim 1, wherein the one or more processors are further configured to execute the instructions to:

increase a size of another ultrasound preview image that is adjacent to the ultrasound preview image.

8. A method comprising:

displaying a plurality of ultrasound preview images that correspond to one or more previous exams of a subject on a display of an ultrasound system;

determining a gaze location of a user on the display of the ultrasound system;

determining an ultrasound preview image, from among the plurality of ultrasound preview images, that corresponds to the gaze location of the user on the display of the ultrasound system; and increasing a size of the ultrasound preview image based on determining the ultrasound preview image that corresponds to the gaze location of the user on the display of the ultrasound system.

9. The method of claim 8, further comprising:

determining that another gaze location of the user on the display of the ultrasound system corresponds to an end of a list of the plurality of ultrasound preview images; and scrolling through the list of the plurality of ultrasound preview images based on determining that the other gaze location of the user on the display of the ultrasound system corresponds to the end of the list of the plurality of ultrasound preview images.

10. The method of claim 8, further comprising:

beginning playback of an ultrasound video corresponding to the ultrasound preview image based on displaying the ultrasound preview image in a final size.

11. The method of claim 8, further comprising:

maintaining positions of other ultrasound preview images that do not correspond to the gaze location of the user.

12. The method of claim 8, further comprising:

decreasing sizes of other ultrasound preview ultrasound images that do not correspond to the gaze location of the user.

13. The method of claim 8, further comprising:

removing a display of other ultrasound preview ultrasound images that do not correspond to the gaze location of the user.

14. The method of claim 8, further comprising:

increasing a size of another ultrasound preview image that is adjacent to the ultrasound preview image.

15. A non-transitory computer-readable medium storing instructions that, when executed by one or more processors, cause the one or more processors to:

display a plurality of ultrasound preview images that correspond to one or more previous exams of a subject on a display of the ultrasound system;

determine a gaze location of a user on the display of the ultrasound system;

determine an ultrasound preview image, from among the plurality of ultrasound preview images, that corresponds to the gaze location of the user on the display of the ultrasound system; and increase a size of the ultrasound preview image based on determining the ultrasound preview image that corresponds to the gaze location of the user on the display of the ultrasound system.

16. The non-transitory computer-readable medium of claim 15, wherein the instructions further cause the one or more processors to:

determine that another gaze location of the user on the display of the ultrasound system corresponds to an end of a list of the plurality of ultrasound preview images; and scroll through the list of the plurality of ultrasound preview images based on determining that the other gaze location of the user on the display of the ultrasound system corresponds to the end of the list of the plurality of ultrasound preview images.

17. The non-transitory computer-readable medium of claim 15, wherein the instructions further cause the one or more processors to:

begin playback of an ultrasound video corresponding to the ultrasound preview image based on displaying the ultrasound preview image in a final size.

18. The non-transitory computer-readable medium of claim 15, wherein the instructions further cause the one or more processors to:

maintain positions of other ultrasound preview images that do not correspond to the gaze location of the user.

19. The non-transitory computer-readable medium of claim 15, wherein the instructions further cause the one or more processors to:

decrease sizes of other ultrasound preview ultrasound images that do not correspond to the gaze location of the user.

20. The non-transitory computer-readable medium of claim 15, wherein the instructions further cause the one or more processors to:

remove a display of other ultrasound preview ultrasound images that do not correspond to the gaze location of the user.

21. The non-transitory computer-readable medium of claim 15, wherein the instructions further cause the one or more processors to:

increase a size of another ultrasound preview image that is adjacent to the ultrasound preview image.

* * * * *